(12) United States Patent
Aristizabal et al.

(10) Patent No.: US 10,695,206 B2
(45) Date of Patent: *Jun. 30, 2020

(54) ENDOLUMINAL PROSTHESIS DEPLOYMENT DEVICES AND METHODS

(71) Applicant: TRIVASCULAR, INC., Santa Rosa, CA (US)

(72) Inventors: Diego Aristizabal, Santa Rosa, CA (US); Dale L Ehnes, Sebastopol, CA (US); Teresa Woodson, Windsor, CA (US)

(73) Assignee: TRIVASCULAR, INC., Santa Rosa, CA (US)

( * ) Notice: Subject to any disclaimer, the term of this patent is extended or adjusted under 35 U.S.C. 154(b) by 156 days.

This patent is subject to a terminal disclaimer.

(21) Appl. No.: 15/737,881

(22) PCT Filed: Jul. 28, 2016

(86) PCT No.: PCT/US2016/044583
§ 371 (c)(1),
(2) Date: Dec. 19, 2017

(87) PCT Pub. No.: WO2017/019913
PCT Pub. Date: Feb. 2, 2017

(65) Prior Publication Data
US 2018/0296378 A1    Oct. 18, 2018

Related U.S. Application Data

(60) Provisional application No. 62/199,168, filed on Jul. 30, 2015, provisional application No. 62/201,046, filed on Aug. 4, 2015.

(51) Int. Cl.
*A61F 2/966* (2013.01)
*A61F 2/95* (2013.01)
*A61F 2/07* (2013.01)

(52) U.S. Cl.
CPC ........... *A61F 2/966* (2013.01); *A61F 2/95* (2013.01); *A61F 2002/072* (2013.01);
(Continued)

(58) Field of Classification Search
CPC .... A61F 2/966; A61F 2/95; A61F 2002/9511; A61F 2002/9534; A61F 2210/0014; A61F 2002/9665; A61F 2002/072
(Continued)

(56) References Cited

U.S. PATENT DOCUMENTS

| 5,047,045 A | 9/1991 | Arney et al. |
| 5,158,548 A | 10/1992 | Lau et al. |

(Continued)

FOREIGN PATENT DOCUMENTS

| EP | 0621016 | 10/1994 |
| EP | 1327422 | 7/2003 |

(Continued)

OTHER PUBLICATIONS

International Search Report and Written Opinion dated Feb. 2, 2016 in International Patent Application No. PCT/US2015/057016 filed: Oct. 22, 2015 and published as: WO/2016/065208 on: Apr. 28, 2016.
(Continued)

*Primary Examiner* — Julian W Woo
(74) *Attorney, Agent, or Firm* — Foley & Lardner LLP

(57) ABSTRACT

Catheter systems and methods for deployment of an endoluminal prosthesis in a body lumen of a patient while maintaining control of a position of the endoluminal prosthesis during the deployment process. Some of the systems and methods are configured to minimize frictional forces of components of the catheter systems during deployment procedures.

19 Claims, 20 Drawing Sheets

(52) U.S. Cl.
CPC ............... *A61F 2002/9511* (2013.01); *A61F 2002/9534* (2013.01); *A61F 2002/9665* (2013.01); *A61F 2210/0014* (2013.01)

(58) Field of Classification Search
USPC .............................................. 623/1.11, 1.46
See application file for complete search history.

(56) References Cited

U.S. PATENT DOCUMENTS

| | | | |
|---|---|---|---|
| 5,354,310 A | 10/1994 | Carnic et al. | |
| 5,445,646 A | 8/1995 | Euteneuer et al. | |
| 5,480,423 A | 1/1996 | Ravenscroft et al. | |
| 5,534,007 A | 7/1996 | St. Germain et al. | |
| 5,571,087 A | 11/1996 | Ressemann et al. | |
| 5,605,543 A | 2/1997 | Swanson | |
| 5,662,703 A | 9/1997 | Yurek et al. | |
| 5,683,451 A | 11/1997 | Lenker et al. | |
| 5,683,452 A | 11/1997 | Barone et al. | |
| 5,749,921 A * | 5/1998 | Lenker ...................... | A61F 2/95 606/194 |
| 5,824,058 A | 10/1998 | Ravenscroft et al. | |
| 6,077,297 A | 6/2000 | Robinson | |
| 6,126,685 A | 10/2000 | Lenker et al. | |
| 6,251,132 B1 | 6/2001 | Ravenscroft | |
| 6,344,044 B1 | 2/2002 | Rulkerson et al. | |
| 6,395,018 B1 | 5/2002 | Castaneda | |
| 6,428,566 B1 | 8/2002 | Holt | |
| 6,463,317 B1 | 10/2002 | Kucharczky et al. | |
| 6,582,460 B1 | 6/2003 | Cryer | |
| 6,660,030 B2 | 12/2003 | Shaolian et al. | |
| 7,255,711 B2 | 8/2007 | Holman et al. | |
| 7,284,399 B1 | 10/2007 | Sisco | |
| 7,338,518 B2 | 3/2008 | Chobotov | |
| 7,722,663 B1 | 5/2010 | Austin | |
| 7,998,189 B2 | 8/2011 | Kolbel et al. | |
| 8,007,605 B2 * | 8/2011 | Arbefeuille ............... | A61F 2/07 148/563 |
| 8,066,755 B2 | 11/2011 | Zacharias et al. | |
| 8,206,427 B1 | 6/2012 | Ryan et al. | |
| 8,764,811 B2 * | 7/2014 | Rea Peterson ............ | A61F 2/95 623/1.11 |
| 8,801,769 B2 | 8/2014 | Chobotov | |
| 9,364,314 B2 | 6/2016 | Berra et al. | |
| 9,393,115 B2 * | 7/2016 | Tabor ...................... | A61F 2/2412 |
| 9,532,872 B2 * | 1/2017 | Salahieh ............ | A61B 17/0644 |
| 2001/0023369 A1 | 9/2001 | Chobotov | |
| 2001/0037142 A1 | 11/2001 | Stelter et al. | |
| 2001/0047150 A1 | 11/2001 | Chobotov | |
| 2001/0049509 A1 | 12/2001 | Sekine et al. | |
| 2002/0040236 A1 | 4/2002 | Lau et al. | |
| 2002/0156521 A1 | 10/2002 | Ryan et al. | |
| 2002/0188344 A1 | 12/2002 | Bolea et al. | |
| 2003/0199967 A1 | 10/2003 | Hartley et al. | |
| 2004/0044358 A1 | 3/2004 | Khosravi et al. | |
| 2004/0064083 A1 | 4/2004 | Becker | |
| 2004/0138734 A1 | 7/2004 | Chobotov et al. | |
| 2004/0148008 A1 | 7/2004 | Goodson, IV et al. | |
| 2004/0176836 A1 | 9/2004 | Kari et al. | |
| 2005/0004660 A1 | 1/2005 | Rosenbluth et al. | |
| 2006/0009833 A1 | 1/2006 | Chobotov et al. | |
| 2007/0016281 A1 | 1/2007 | Melsheimer | |
| 2007/0078506 A1 | 4/2007 | McCormick et al. | |
| 2008/0208240 A1 | 8/2008 | Paz | |
| 2008/0264102 A1 | 10/2008 | Berra | |
| 2008/0312671 A1 | 12/2008 | Riles et al. | |
| 2009/0082845 A1 | 3/2009 | Chobotov | |
| 2009/0125098 A1 | 5/2009 | Chuter | |
| 2009/0187240 A1 * | 7/2009 | Clerc ...................... | A61F 2/07 623/1.17 |
| 2010/0174354 A1 | 7/2010 | Hyodoh et al. | |
| 2010/0234932 A1 | 9/2010 | Arbefeuille et al. | |
| 2010/0249908 A1 | 9/2010 | Chau et al. | |
| 2010/0286760 A1 | 11/2010 | Beach et al. | |
| 2011/0178588 A1 | 7/2011 | Haselby | |
| 2012/0191174 A1 | 7/2012 | Vinluan et al. | |
| 2013/0261734 A1 | 10/2013 | Young et al. | |
| 2013/0268048 A1 | 10/2013 | Watson et al. | |
| 2013/0268056 A1 | 10/2013 | Chobotov et al. | |
| 2013/0268057 A1 | 10/2013 | Vinluan et al. | |
| 2013/0338753 A1 | 12/2013 | Geusen | |
| 2014/0107758 A1 | 4/2014 | Glazier | |
| 2015/0073523 A1 | 3/2015 | Chobotov | |
| 2015/0164667 A1 | 6/2015 | Vinluan et al. | |

FOREIGN PATENT DOCUMENTS

| | | |
|---|---|---|
| JP | 18-136382 | 6/2006 |
| WO | WO 96/014808 | 5/1996 |
| WO | WO 97/017898 | 5/1997 |
| WO | WO 01/056504 | 8/2001 |
| WO | WO 01/058387 | 8/2001 |
| WO | WO 01/076509 | 10/2001 |
| WO | WO 04/019823 | 3/2004 |
| WO | WO 05/115275 | 12/2005 |
| WO | WO 09/064923 | 5/2009 |
| WO | WO 09/132309 | 10/2009 |
| WO | WO 12/068175 | 5/2012 |
| WO | WO 16/065208 | 4/2016 |
| WO | WO 16/191602 | 12/2016 |
| WO | WO 17/019913 | 2/2017 |

OTHER PUBLICATIONS

International Search Report and Written Opinion dated Sep. 12, 2016 in International Patent Application No. PCT/US2016/034427 filed: May 26, 2016 and published as: WO/2016/191602 on Dec. 1, 2016.

International Search Report and Written Opinion dated Dec. 1, 2016 in International Patent Application No. PCT/US2016/044583 filed: Jul. 28, 2016 and published as: WO/2017/019913 on: Feb. 2, 2017.

International Search Report and Written Opinion dated Jun. 12, 2012 in International Patent Application No. PCT/US2011/060873 filed: Nov. 15, 2011 and published as: WO/2012/068175 on: May 24, 2012.

Extended European Search Report dated Jan. 27, 2015 in European Application No. EP 11841183.4 filed: Nov. 15, 2011.

Supplemental European Search Report dated Feb. 13, 2015 in European Application No. EP 11841183.4 filed: Nov. 15, 2011.

Extended European Search Report dated Feb. 14, 2019, from application No. 16831382.3.

* cited by examiner

ENDOLUMINAL PROSTHESIS DEPLOYMENT DEVICES AND METHODS

RELATED APPLICATIONS

This application is a national stage application under 35 U.S.C. section 371 of International Patent Application No. PCT/US2016/044583, filed Jul. 28, 2016, naming Diego Aristizabal et al. as inventors, entitled ENDOLUMINAL PROSTHESIS DEPLOYMENT DEVICES AND METHODS, which claims priority from U.S. Provisional Patent Application Ser. No. 62/199,168, filed Jul. 30, 2015, by D. Ehnes and titled "Stent Graft Deployment Devices and Methods Using Double-Backed Sheath", and U.S. Provisional Patent Application Ser. No. 62/201,046, filed Aug. 4, 2015, by T. Woodson et al. and titled "Stent Retention Mechanisms and Methods for Endoluminal Prosthesis Delivery", all of which are incorporated by reference herein in their entirety.

BACKGROUND

An aneurysm is a vascular defect indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs. An example of a surgical procedure involving repair of an AAA is described in a book titled Surgical Treatment of Aortic Aneurysms by Denton A. Cooley, M. D., published in 1986 by W. B. Saunders Company.

Due to the inherent risks and complexities of surgical repair of aortic aneurysms, minimally invasive endovascular repair has become a widely-used alternative therapy, most notably in treating AAAs. Early work in this field is exemplified by Lawrence, Jr. et al. in "Percutaneous Endovascular Graft: Experimental Evaluation", Radiology (May 1987) and by Mirich et al. in "Percutaneously Placed Endovascular Grafts for Aortic Aneurysms: Feasibility Study," Radiology (March 1989).

When deploying endoluminal prosthesis type devices by catheter or other suitable instrument, it may be advantageous to have a flexible and low profile endoluminal prosthesis such as a stent graft and catheter system for passage through the various guiding catheters as well as the patient's sometimes tortuous anatomy. Many of the existing endovascular prostheses and methods for treatment of aneurysms as well as other indications within body lumens of patients, while representing significant advancement over previous devices and methods, use systems having relatively large transverse profiles, often up to 24 French. Also, such existing systems may have greater than desired lateral stiffness, which can complicate the delivery process, particularly for use in treatment of vascular defect sites that include a high degree of curvature or angulation. Even with more flexible low profile delivery systems, deployment of endovascular prostheses in highly angulated and curved vessels may be problematic due to difficulties with visualization or imaging of the orientation of the prostheses during the deployment process. In addition, such angulated or tortuous anatomies may also induce undesirable amounts of friction between components of catheter systems that may make operation of the catheter system challenging in some situations. As such, minimally invasive endovascular treatment of aneurysms as well as other indications within a body lumen of a patient may not be available for many patients that would benefit from such a procedure and can be more difficult to carry out for those patients for whom the procedure is indicated.

What have been needed are catheter systems and methods of using these catheter systems that are adaptable to a wide range of patient anatomies such that suitable endoluminal prostheses may be safely and reliably deployed using a flexible low profile catheter system.

SUMMARY

Some embodiments of a catheter system for deploying an endoluminal prosthesis in a body lumen of a patient include a flexible elongate chassis having a proximal end, a distal end, a distal section and an overall column strength sufficient for advancement of the chassis through a body lumen of a patient. The catheter system may also include a self-expanding tubular endoluminal prosthesis disposed in a constrained state over the distal section of the chassis. In addition, such a catheter system may include a thin, flexible, resilient extension including a proximal end which is secured in fixed relation to the elongate catheter chassis and a distal end which is disposed radially outward from an outside surface of the chassis and distal of the proximal end of the extension. For such a catheter system, the extension may extend through a wall of a distal end of the endoluminal prosthesis with the extension in a radially constrained state such that the extension at least partially captures a distal segment of the endoluminal prosthesis and restricts proximal displacement of the endoluminal prosthesis relative to the chassis. In some cases, such a catheter system may include a plurality of such extensions.

Some embodiments of a catheter system for deploying an endoluminal prosthesis in a body lumen of a patient include a flexible elongate chassis having a proximal end, a distal end, a distal section and an overall column strength sufficient for advancement of the chassis through a body lumen of a patient. The catheter system may also include a self-expanding tubular endoluminal prosthesis disposed in a constrained state over the distal section of the chassis. In addition, the catheter system may also include a rigid extension having a proximal end which is secured in fixed relation to the elongate catheter chassis, and a distal end which is disposed radially outward from an outside surface of the chassis and distal of the proximal end of the extension. For such a catheter system, the extension may extend through a wall of a distal end of the endoluminal prosthesis with the extension in a radially constrained state such that the extension at least partially captures a distal segment of the endoluminal prosthesis and restricts proximal displacement of the endoluminal prosthesis relative to the chassis. In some cases, such a catheter system may include a plurality of such rigid extensions.

Some embodiments of a method for deploying an endoluminal prosthesis in a body lumen of a patient include advancing a catheter system for deployment of an endoluminal prosthesis into the body lumen of the patient until the endoluminal prosthesis of the catheter system is disposed at a treatment site. An outer constraint may then be removed from the endoluminal prosthesis while an extension prevents proximal axial movement of the endoluminal prosthesis relative to the chassis. Such an extension may include a proximal end which is secured in fixed relation to an elongate catheter chassis and a distal end which is disposed radially outward from an outside surface of the chassis and distal of the proximal end of the extension. The extension also extends through a wall of a distal end of the endoluminal prosthesis with the extension in a radially constrained state such that the extension at least partially captures a distal segment of the endoluminal prosthesis. The endoluminal prosthesis is then allowed to self-expand such that an outside surface of the endoluminal prosthesis contacts an inside surface of the patient's body lumen. The chassis and extension may then be proximally retracted such that the extension passes axially through the wall of the distal end of the endoluminal prosthesis and fully disengages the endoluminal prosthesis.

Some embodiments of a catheter system for deploying an endoluminal prosthesis in a body lumen of a patient include a flexible elongate chassis having a proximal end, a distal end, a distal section and an overall column strength sufficient for advancement of the chassis through a body lumen of a patient. Such a catheter system may also include a self-expanding tubular endoluminal prosthesis disposed in a constrained state over the distal section of the chassis. In addition, such a catheter system may include a thin, flexible, axial belt having a fixed end which is secured in fixed relation to the elongate catheter chassis and a free end which is disposed opposite the fixed end. For such catheter system embodiments, the axial belt may form a loop that extends proximally from the fixed end and free end through a distal segment of a wall of the endoluminal prosthesis. The free end of the axial belt is releasably secured in fixed relation to the chassis with a circumferential belt which is disposed about the chassis and free end such that the loop captures a distal segment of the endoluminal prosthesis and restricts proximal displacement of the endoluminal prosthesis relative to the chassis.

Some embodiments of a method for deploying an endoluminal prosthesis in a body lumen of a patient include advancing a catheter system for deployment of an endoluminal prosthesis into the body lumen of the patient until the endoluminal prosthesis of the catheter system is disposed at a treatment site. An outer constraint may be removed from the endoluminal prosthesis while an axial belt restricts proximal axial movement of the endoluminal prosthesis relative to the chassis. Such an axial belt may include a fixed end which is secured in fixed relation to the elongate catheter chassis and a free end which is disposed opposite the fixed end. The axial belt forms a loop that extends proximally from the fixed end and free end through a distal segment of a wall of the endoluminal prosthesis with the free end of the axial belt releasably secured in fixed relation to the chassis with a circumferential belt which is disposed about the chassis and free end such that the loop captures a distal segment of the endoluminal prosthesis. The endoluminal prosthesis may be allowed to self-expand by removal of the constraint such that an outside surface of the endoluminal prosthesis contacts an inside surface of the patient's body lumen. The circumferential belt is then released from the axial belt and axial belt from the distal segment of the endoluminal prosthesis so as to allow the endoluminal prosthesis to be fully deployed and engage the body lumen.

The chassis and axial belt may then be proximally retracted such that the axial belt is withdrawn from the wall of the distal end of the endoluminal prosthesis.

Some embodiments of a catheter system for deploying an endoluminal prosthesis in a body lumen of a patient include a flexible elongate chassis having a proximal end, a distal end, a distal section and an overall column strength sufficient for advancement of the chassis through a body lumen of a patient. Such a catheter system may also include a self-expanding tubular endoluminal prosthesis disposed in a constrained state over the distal section of the chassis. In addition, such a catheter system may include a plurality of axial release wires, with each axial release wire having a proximal end, a distal end and a distal section. For such an embodiment, the distal section of each release wire may extend through a distal segment of a wall of the endoluminal prosthesis with the distal section releasably secured in fixed relation to a pair of axially spaced bushings which are secured to and extend radially outward from the chassis. Such a structure may be configured so as to form a loop structure or otherwise enclosed structure between the distal section, the axially spaced bushings and an outside surface of the chassis, such that this loop structure releasably captures a distal segment of the endoluminal prosthesis and restricts proximal displacement of the endoluminal prosthesis relative to the chassis.

Some embodiments of a catheter system for deploying an endoluminal prosthesis in a body lumen of a patient include a flexible elongate chassis having a proximal end, a distal end, and a column strength configured for advancement of the chassis through a body lumen of a patient. Such a catheter system may also include a self-expanding tubular endoluminal prosthesis disposed in a constrained state at the distal end of the chassis. In addition, such a catheter system may include a tubular everting sheath which has an inner section which includes a first diameter, a fixed end which is secured in fixed relation to the chassis and an endoluminal prosthesis section that is disposed over and radially constrains the endoluminal prosthesis in the constrained state. The tubular everting sheath may also have an outer section that is everted back over the endoluminal prosthesis section of the inner portion. The outer section may include a retraction end and a second diameter which is larger than the first diameter of the inner section such that the outer section is readily slideable over the inner section during retraction of the retraction end and eversion of the everting sheath.

Some embodiments of a catheter system for deploying an endoluminal prosthesis in a body lumen of a patient may include a flexible elongate chassis having a proximal end, a distal end, and a column strength configured for advancement of the chassis through a body lumen of a patient. Such a catheter system may also include a self-expanding tubular endoluminal prosthesis disposed in a constrained state at the distal end of the chassis. In addition, such a catheter system may include a tubular everting sheath which has an inner section which includes a fixed end which is secured in fixed relation to the chassis and an endoluminal prosthesis section that is disposed over and radially constrains the endoluminal prosthesis in the constrained state. The tubular everting sheath may also have an outer section that is everted back over the endoluminal prosthesis section of the inner portion. The outer section may also include a retraction end. The everting sheath may also include a PTFE material having a closed cell microstructure with no distinct fibrils interconnecting adjacent nodes such that the outer section is readily slideable over the inner section.

Some embodiments of a method for deploying an endoluminal prosthesis in a body lumen of a patient include advancing a catheter system for deployment of an endoluminal prosthesis into the body lumen of the patient until the endoluminal prosthesis of the catheter system is disposed at a treatment site in a constrained state. The endoluminal prosthesis is held in the constrained state by an endoluminal prosthesis section of an inner section of a tubular everting sheath. In some cases, the inner section may have a first diameter and a fixed end which is secured in fixed relation to an elongate chassis of the catheter system. An outer constraint may be removed from the endoluminal prosthesis by proximally retracting a retraction end of an outer section of the tubular everting sheath. Such an outer section may be everted back over the endoluminal prosthesis section of the inner section and include a second diameter which is larger than the first diameter of the inner section. The endoluminal prosthesis may be thus allowed to self-expand as the endoluminal prosthesis section of the inner section is proximally everted so as to remove radial constraint from the endoluminal prosthesis. As the endoluminal prosthesis self-expands, an outside surface of the endoluminal prosthesis may then engage an inside surface of the patient's body lumen.

Some embodiments of a method for deploying an endoluminal prosthesis in a body lumen of a patient include advancing a catheter system for deployment of an endoluminal prosthesis into the body lumen of the patient until the endoluminal prosthesis of the catheter system is disposed at a treatment site in a constrained state. For such a catheter system, the endoluminal prosthesis may be held in the constrained state by an endoluminal prosthesis section of an inner section of a tubular everting sheath. Such a tubular everting sheath may include a PTFE material having a closed cell microstructure with no distinct fibrils interconnecting adjacent nodes. The inner section may include a fixed end which is secured in fixed relation to an elongate chassis of the catheter system. An outer constraint may then be removed from the endoluminal prosthesis by proximally retracting a retraction end of an outer section of the tubular everting sheath. Such an outer section may be everted back over the endoluminal prosthesis section of the inner section. The endoluminal prosthesis may then be allowed to self-expand as the endoluminal prosthesis section of the inner section is proximally everted so as to remove radial constraint from the endoluminal prosthesis. As the endoluminal prosthesis self-expands, an outside surface of the endoluminal prosthesis may engage an inside surface of the patient's body lumen.

Some embodiments of a catheter system for deploying an endoluminal prosthesis in a body lumen of a patient may include a flexible elongate chassis having a proximal end, a distal end, a distal section and an overall column strength sufficient for advancement of the chassis through a body lumen of a patient. The catheter system may also include a self-expanding tubular endoluminal prosthesis disposed in a constrained state over the distal section of the chassis and a thin, flexible, resilient extension that extends through a wall of a distal end of the endoluminal prosthesis. The extension may be disposed in a radially constrained state such that the extension at least partially captures a distal segment of the endoluminal prosthesis and restricts proximal displacement of the endoluminal prosthesis relative to the chassis. The extension may include a proximal end which is secured in fixed relation to the elongate catheter chassis and a distal end which is disposed radially outward from an outside surface of the chassis and distal of the proximal end of the extension. In addition, the catheter system may further include a tubular everting sheath which has an inner section which includes a fixed end which is secured in fixed relation to the chassis and an endoluminal prosthesis section that is disposed over and radially constrains the endoluminal prosthesis and extension in the constrained state. The tubular everting outer sheath may also have an outer section that is everted back over the endoluminal prosthesis section of the inner portion, the outer section including a retraction end which is disposed at an opposite end of the everting sheath relative to the fixed end.

Some embodiments of a method for deploying an endoluminal prosthesis in a body lumen of a patient may include advancing a catheter system for deployment of an endoluminal prosthesis into the body lumen of the patient until the endoluminal prosthesis of the catheter system is disposed at a treatment site. For such a catheter system, the endoluminal prosthesis and a resilient, flexible, extension that at least partially captures a distal segment of the endoluminal prosthesis may both be held in a constrained state by an endoluminal prosthesis section of an inner section of a tubular everting sheath. An outer constraint may thereafter be removed from the endoluminal prosthesis and the extension by proximally retracting a retraction end of an outer section of the tubular everting sheath. Retraction of the outer section may be carried out by the outer section being everted back over the endoluminal prosthesis section of the inner section during the proximal retraction while the extension prevents proximal axial movement of the endoluminal prosthesis relative to a flexible, elongate chassis of the catheter system. The endoluminal prosthesis and extension may then be allowed to self-expand such that an outside surface of the endoluminal prosthesis engages an inside surface of the patient's body lumen. Finally, the chassis and extension may be proximally retracted such that the extension passes axially through the wall of the distal end of the endoluminal prosthesis and no longer engages the distal segment of the endoluminal prosthesis.

Some embodiments of a method of loading an endoluminal prosthesis into a sheath which is configured to constrain the endoluminal prosthesis include passing a plurality of thin high tensile tethers loops through an end of the endoluminal prosthesis. The plurality of tether loops is also passed through an inner lumen of the sheath. An end of the sheath is restrained and both ends of each of the tether loops are pulled on simultaneously in a direction away from the endoluminal prosthesis such that the tether loops are pulled through the inner lumen of the sheath and axial tension is thereby applied to the end of the endoluminal prosthesis such that the endoluminal prosthesis is radially compressed and constrained as it is pulled into a funnel section of the inner lumen of the sheath to an endoluminal prosthesis section within the inner lumen of the sheath. Thereafter, only one side of each of the tether loops is pulled on and an opposite end of each tether loop is released until each of the tether loops is pulled out of the endoluminal prosthesis and the inner lumen of the sheath.

Certain embodiments are described further in the following description, examples, claims and drawings. These features of embodiments will become more apparent from the following detailed description when taken in conjunction with the accompanying exemplary drawings.

Figure 1:
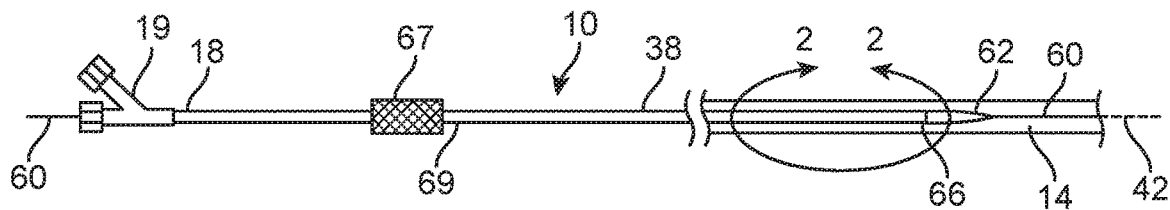
FIG. 1 is an elevation view of a catheter system for deploying an endoluminal prosthesis in a body lumen of a patient disposed in a body lumen.

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

As discussed above, there is a need for catheter systems for deployment of endoluminal prostheses that can reliably and accurately deliver such devices to a wide variety of body lumen target sites within a patient. In order to achieve this, it may be desirable to configure catheter system embodiments to maintain control of an axial position of an endoluminal prosthesis during deployment in order to maintain accuracy. It may also be desirable to minimize frictional forces within the various components of catheter system embodiments such that the catheter system embodiments function readily even in difficult to access and tortuous anatomies. In addition, minimizing frictional forces may be important when accessing body lumen target sites that are spatially remote from a point of access to the patient's body. Various catheter system embodiments are discussed herein that may be directed to achieving one or more such desirable attributes. In addition, various methods of using such catheter systems or methods of preparing or manufacturing such catheter systems are also discussed. With regard to terms used to describe the orientation of the various catheter systems discussed herein, the term "distal" is used to describe a position or direction away from a user of a catheter system and the term "proximal" is used to describe a position or direction towards a user of a catheter system. The same convention also applies to endoluminal prostheses components of such catheter systems. Although it is common to describe a "proximal" end of endoluminal prosthesis devices as being that end which is disposed towards a flow of blood of a patient, this convention is not adopted herein.

Referring to FIGS. 1-10, a catheter system 10 is shown that is configured to control an axial position of a self-expanding endoluminal prosthesis 12 during deployment. In particular, the catheter system 10 for deploying the endoluminal prosthesis 12 in a body lumen 14 of a patient is shown which may include a flexible elongate chassis 16 having a proximal end 18, a distal end 20, a distal section 22 and an overall column strength configured for advancement of the chassis 16 through a body lumen 14 of a patient. In some cases, the elongate chassis 16 may be configured for atraumatic passage through tortuous body lumens 14 of a patient, such as tortuous arteries or veins of a patient's vasculature. The chassis may have any suitable configuration that provides both a sufficient flexibility in order to navigate a patient's body lumens 14 and structural strength in order to support the various structures secured thereto and functions carried out with the chassis 16. In some cases, the chassis may include an elongate tubular structure made from any suitable biocompatible polymer such as polyurethane, polytetrafluoroethylene (PTFE), polyethylene (PE), nylon, Pebax®, fluorinated ethylene propylene (FEP), polyimides, composite materials or the like.

Figure 2:
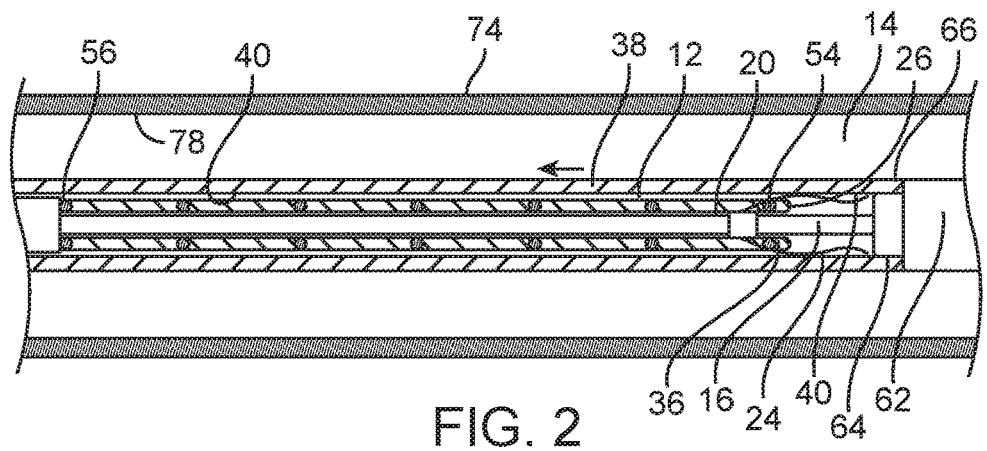
FIG. 2 is an enlarged view in partial section of the catheter system and body lumen indicated by the encircled portion 2-2 of FIG. 1.

The self-expanding tubular endoluminal prosthesis 12 is shown disposed in a constrained state over the distal section of the chassis 16 with proximal axial displacement of the endoluminal prosthesis 12 being restricted by a plurality of extensions 24 that extend from the chassis 16 through a distal end 26 of the endoluminal prosthesis 12. The proximal axial displacement of the endoluminal prosthesis 12 may be so restricted by one or more such extensions 24. Each extension 24 may be a thin, flexible, resilient extension having a proximal end 28 which is secured in fixed relation to the elongate catheter chassis 16 and a distal end 30 which is disposed radially outward from an outside surface 32 of the chassis 16 and distal of the proximal end 28 of the extension 24. The fixation of the proximal end 28 relative to the chassis may be facilitated by a base structure such as a high strength cylinder of material that may or may not be made from the same material as the extension 24. Each of the extensions 24 may extend through a wall 34 of the distal end 26 of the endoluminal prosthesis 12 with the extension 24 in a radially constrained state such that the extension 24 at least partially captures a distal segment 36 of the endoluminal prosthesis 12 and restricts proximal displacement of the endoluminal prosthesis 12 relative to the chassis 16 as shown in FIG. 2. For some embodiments, the catheter system 10 may have 1 extension 24 to 10 extensions 24, more specifically, 2 extensions 24 to 6 extensions 24, and even more specifically, 3 extensions 24 to 4 extensions 24.

Figure 8:
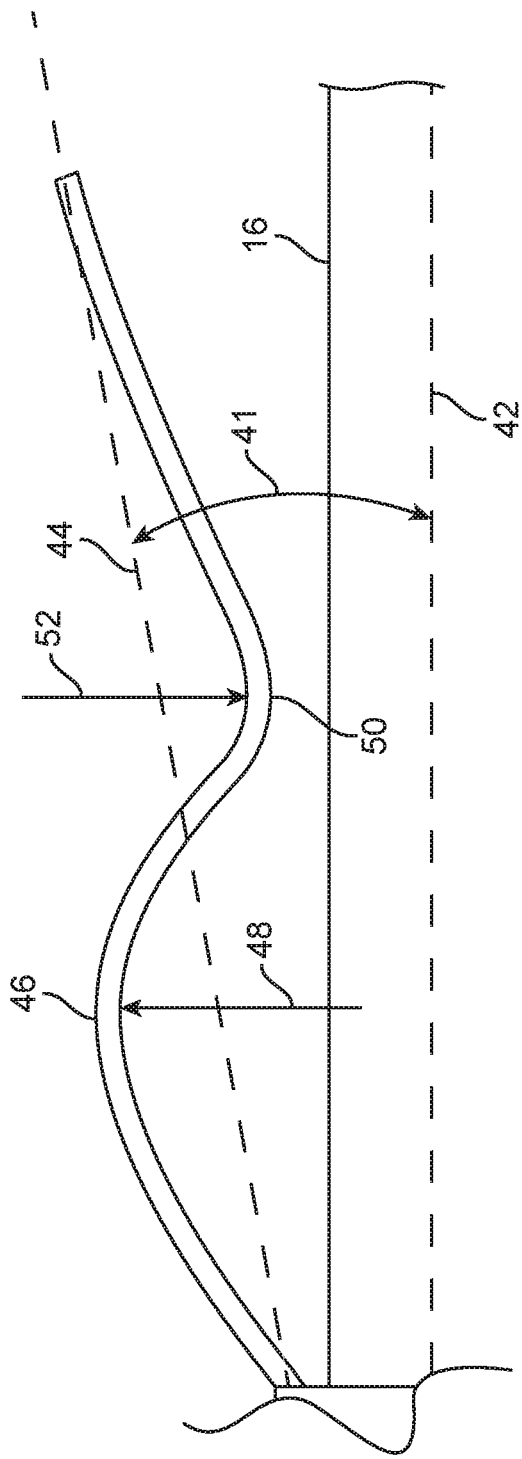
FIG. 8 is an enlarged elevation view of an extension embodiment.

The catheter system 10 may optionally include a tubular outer sheath 38 which is disposed over the endoluminal prosthesis 12 and chassis 16 and which includes an inner surface 40 that constrains the endoluminal prosthesis 12 in the constrained state. The inner surface 40 of the outer sheath may also be configured to radially restrain distal ends 30 of the extensions 24 in a radially constrained state as shown in FIG. 2. Such a radially constrained state of the extensions 24 provides more leverage for the extensions 24 to restrict proximal axial movement of the endoluminal prosthesis 12 because the radial constraint on the distal ends 30 of the extensions 24 prevents them from pivoting in a proximal direction when proximal tension is applied to the endoluminal prosthesis 12. As such, for some embodiments, the extensions 24 may have distal ends 30 that extend radially outward from the chassis 16 in a relaxed unconstrained state by a distance similar to a radius of the endoluminal prosthesis 12 to be deployed when that endoluminal prosthesis 12 is also in an unconstrained state. In some instances, an angle 41 that the flexible extensions 24 form with respect to a longitudinal axis 42 of chassis 16 may be about 5 degrees to about 50 degrees with the extension 24 in a relaxed unconstrained state as shown in FIG. 8. The angle 41 of the flexible extensions 24 with respect to the longitudinal axis 42 of the chassis may in some cases be defined by the angle between the longitudinal axis 42 of the chassis 16 and a line 44 extending from the proximal end 28 of the extension 24 to the distal end 30 of the extension 24 as shown in FIG. 8.

Because of the springy resilience of some extension embodiments 24, the distal ends 30 of these extensions 24 may be easily passed through the wall 34 of the endoluminal prosthesis 12 when both the endoluminal prosthesis 12 and the extensions 24 are in a relaxed unconstrained state. Thereafter both the endoluminal prosthesis 12 and the extensions 24 may be radially constrained by an inward radial force and held in that constrained state by an inner surface 40 of the outer sheath 38 as shown in FIG. 2. In order to achieve both a proper flexibility and resilience as well as sufficiently strong bending moment in order to resists failing under an axial load from the endoluminal prosthesis 12 during proximal retraction of the outer sheath 38, some extension embodiments 24 may be made from a resilient high strength material such as a metal alloy or composite material. For some embodiments, the extensions 24 may be made from or include superelastic nickel titanium alloy. For some such embodiments, the extensions 24 may include a transverse cross section area of about 0.08 mm$^2$ to about 1 mm$^2$. For some embodiments, the extensions 24 may have a length of about 4 mm to about 25 mm.

Figure 7:
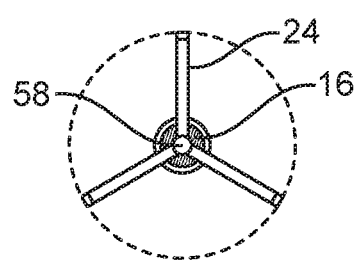
FIG. 7 is a transverse cross section of the elongate chassis of FIG. 6 indicated by lines 7-7 of FIG. 6.

As shown in FIG. 7, the extension 24 lies substantially in a same plane as the longitudinal axis 42 of the chassis 16. In some cases, the meaning of the phrase substantially in the same plane may include lying within a thickness of the extension 24 of lying in the same plane as the longitudinal axis 42 of the chassis 16. For some embodiments, the plurality of extensions 24 is evenly distributed with respect to circumferential orientation about the chassis 16. For example, for such catheter system embodiment 10 having extensions 24, the extensions 24 would be spaced about 120 degrees apart from each other about the longitudinal axis 42 of the chassis 16. In some instances, the extension 24 may have an s-shape in the unconstrained relaxed state as shown in more detail in FIG. 8. For the embodiment shown, a proximal most deflection 46 of the s-shape of the extension 24 extends away from the chassis as indicated by arrow 48 and a distal most deflection 50 of the s-shape of the extension 24 extends towards the chassis as indicated by arrow 52. The outward facing curvature of the proximal most deflection 46 may be useful in order to provide a smooth rounded profile for passage within a constraining tubular structure such as the outer sheath 38 or everting sheath 172 discussed below. The proximal most deflection 46 may also be useful for providing a gap between the outer surface 32 of the chassis and the extensions 24 to accommodate the distal section 36 of the endoluminal prosthesis which may be at least partially mechanically captured by the extension so as to restrict proximal axial movement of the endoluminal prosthesis 12. The optional distal most deflection 50 may be useful in some circumstances for loading the endoluminal prosthesis 12 and distal segments 36 thereof onto the respective extensions 24. The outwardly pointed direction of the proximal ends 28 of the extensions 24 may be useful to facilitate penetration of the extensions 24 through the wall 34 of the endoluminal prosthesis 12 when both the extensions 24 and endoluminal prosthesis 12 are in a relaxed unconstrained state.

Figure 3:
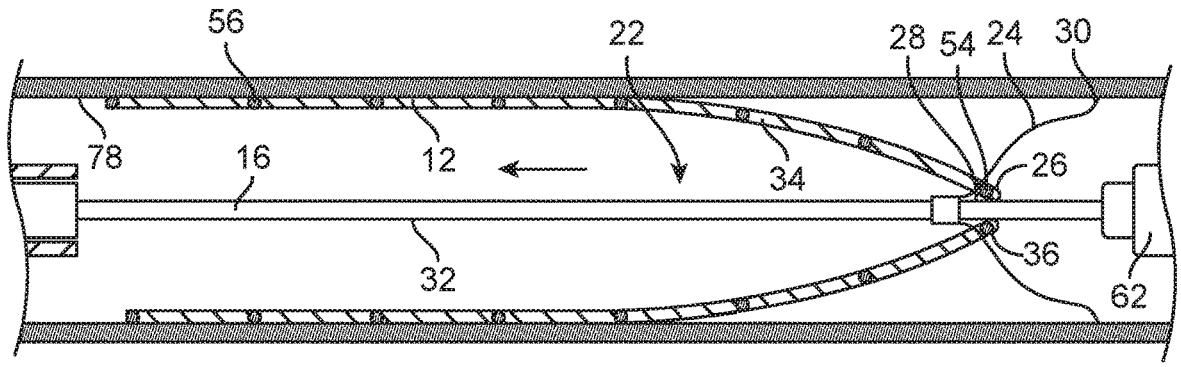
FIG. 3 is an elevation view in partial section of the endoluminal prosthesis of FIG. 2 in a partially deployed state.

For some embodiments, the distal segment 36 of the endoluminal prosthesis 12 captured by the extension 24 may include a high strength stent element 54 of a self-expanding stent 56 of the endoluminal prosthesis 12 as shown in FIGS. 2 and 3. In some cases, the stent element 54 captured by the extension 24 includes a crown section of the stent (not shown). A high strength stent element 54 may include a resilient and optionally superelastic material such as nickel titanium alloy or the like.

For some embodiments, the chassis 16 may optionally include a guidewire lumen 58 to slidably house a guidewire 60 extending from the proximal end 18 of the chassis 16 to the distal end 20 of the chassis 16. In some instances, the catheter system 10 may also include a nosecone 62 secured to a distal end 20 of the chassis 16. The nosecone 62 may include a shoulder portion 64 which is disposed within a distal end 66 of the tubular outer sheath 38 which may also be disposed over the endoluminal prosthesis 12 and chassis 16. The outer sheath 38 includes the inner surface 40 that at least partially radially constrains the endoluminal prosthesis 12 and extensions 24 in the constrained state. For some such embodiments, referring specifically to FIGS. 13-16, the shoulder portion 64 of the nosecone 62 may further optionally include one or more elongate longitudinally oriented slots 68 which are configured to accept the distal end 30 of corresponding extensions 24 when the extensions 24 are in the radially constrained state. Some embodiments of these longitudinally oriented slots 68 may be disposed so as to be substantially parallel to and lie substantially in the same plane as the longitudinal axis 42 of the chassis 16. The longitudinally oriented slots 68 in the nosecone 62 may be useful in some instances for stabilizing the distal ends 30 of the one or more extensions 24 when disposed in the radially constrained state. The distal ends 30 of the extensions may lie in the slots 68 between the nosecone 62 and the inner surface 40 of the outer sheath 38. The slots 68 may, in some instances, make a radial depth of about 0.2 mm to about 3 mm and a circumferential width of about 0.2 mm to about 3 mm. For some embodiments, the slots may have an axial length of about 1 mm to about 10 mm and may in some cases extend all or most of an axial length of the shoulder portion 64.

Figure 9:
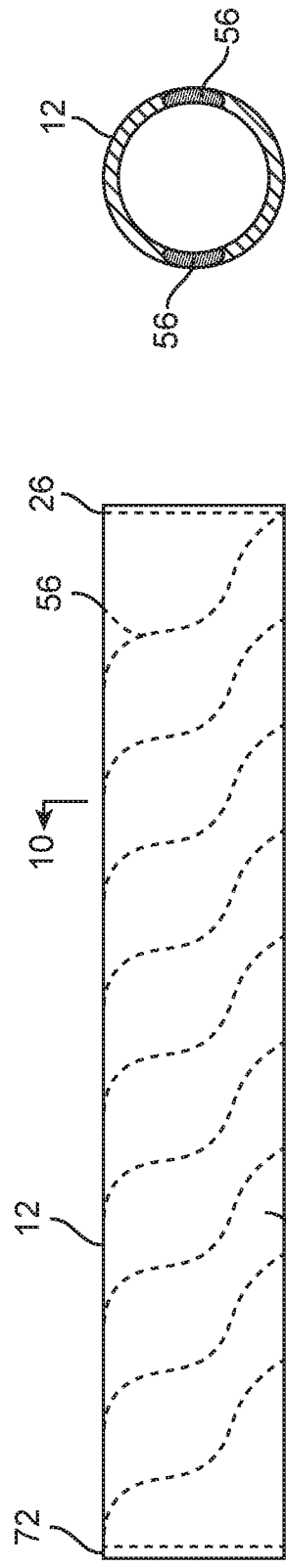
FIG. 9 is an elevation view of an endoluminal prosthesis embodiment as shown in FIGS. 2-5.

In some cases, the tubular endoluminal prosthesis 12 may be a tubular stent graft including at least one layer of thin, compliant material 70 secured to the self-expanding stent 56. For some of these embodiments, the thin compliant material 70 may include nylon mesh, PTFE, ePTFE or the like. In some instances, the stent graft 12 may be a fully stented stent graft as shown in FIG. 9 wherein the helical resilient and undulating stent 56 which is secured to the tubular graft material 70 extends all the way from a distal end 26 of the stent graft to a proximal end of the stent graft. For some embodiments, the endoluminal prosthesis may include a stent 56 made from a high strength superelastic metal alloy such as a nickel titanium or the like.

In use, referring back to FIGS. 1-5, a method embodiment for deploying the endoluminal prosthesis 12 in the body lumen 14 of the patient may include advancing the catheter system 10 into the body lumen 14 of the patient until the endoluminal prosthesis 12 is disposed at a treatment site 74. In some cases, it may be desirable to advance the catheter system 10 to the treatment site over the guidewire 60 which may be previously disposed across a treatment site 74, which may be moved along ahead of the catheter system 10 in a step by step approach or by any other suitable method. Suitable treatment sites 74 for any of the catheter system embodiments 10 and method embodiments discussed herein may include a wide variety of indications such as treatment of vascular defects such as an aneurysm (not shown) or the like or any other suitable indication wherein an endovascular prosthesis 12 may be indicated. In addition, suitable treatment sites 74 may include healthy body lumen sections or substantially healthy body lumen sections that are adjacent to vascular defects. Deployment of endoluminal prostheses in such healthy body lumen sections may be desirable in some cases in order to extend a previously deployed endoluminal prosthesis 12 or for any other suitable indication.

Figure 4:
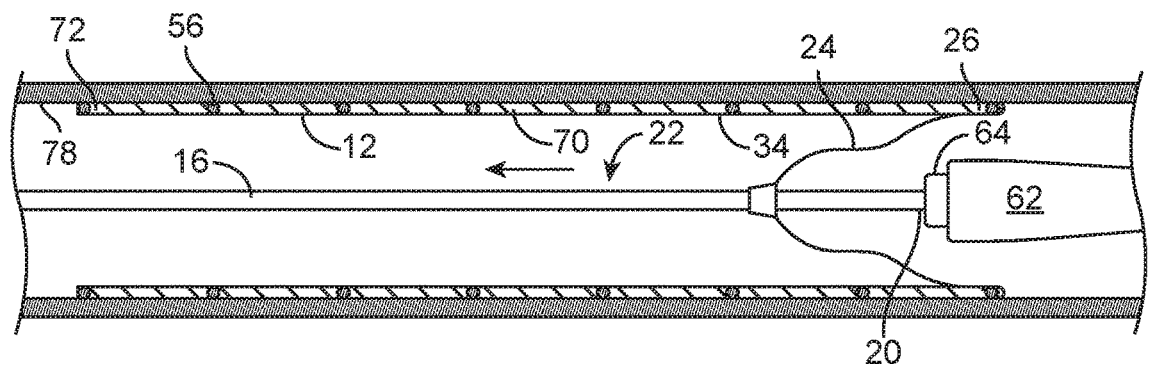
FIG. 4 is an elevation view in partial section of the endoluminal prosthesis of FIG. 2 in a fully deployed state.
Figure 5:
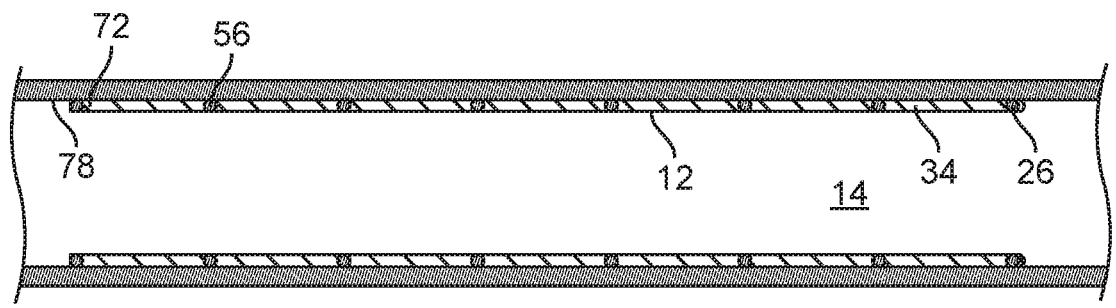
FIG. 5 is an elevation view in partial section of the endoluminal prosthesis of FIG. 2 in a fully deployed state with an elongate chassis and extensions of the catheter system withdrawn from the patient's body lumen.
Figure 6:
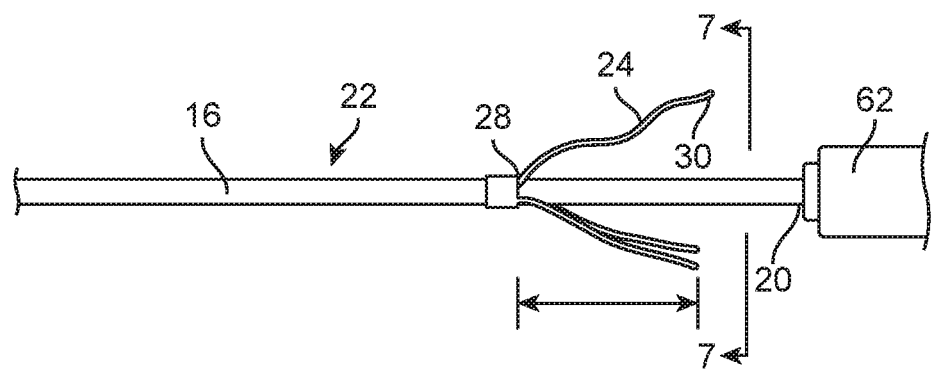
FIG. 6 is an elevation view of the elongate chassis and extensions of a catheter system embodiment.

An outer constraint, such as the outer constraint of the outer sheath 38, may then be removed from the endoluminal prosthesis 12 while the extensions 24 prevent proximal axial movement of the endoluminal prosthesis 12 relative to the chassis 16 due to frictional forces between the outer surface 76 of the endoluminal prosthesis 12 and the inner surface 40 of the outer sheath 38 during proximal retraction of the outer sheath 38. In such cases as shown in FIG. 3, the outer constraint may be removed by proximally retracting the outer sheath 38 of the catheter system 10 which both releases the radial constraint of the outer sheath 38 on the endoluminal prosthesis 12 but also imposes an axial force in a proximal direction on the endoluminal prosthesis 12 due to the frictional interaction between the inner surface 40 of the outer sheath 38 and outside surface 76 of the endoluminal prosthesis 12. An inner transverse dimension of the outer sheath 38 will typically be less than an outer transverse dimension of the endoluminal prosthesis 12 in a relaxed unconstrained state. The extensions 24 may each include the proximal end 28 which is secured in fixed relation to the elongate catheter chassis 16 and the distal end 30 which is disposed radially outward from the outside surface 32 of the chassis 16 and distal of the proximal end 28 of the extension 24 as discussed above. Each of the one or more extensions 24 may also extend through the wall 34 of the distal end 26 of the endoluminal prosthesis 12 with the distal end 30 of the extension 24 held in a radially constrained state by the inner surface 40 of the outer sheath 38, also as discussed above. The extensions 24 are so constrained such that each of the one or more extensions 24 at least partially captures the respective distal segment 36 of the endoluminal prosthesis 12. As the outer constraint is removed, the endoluminal prosthesis 12 is then allowed to self-expand such that an outside surface of the endoluminal prosthesis 12 contacts an inside surface 78 of the patient's body lumen 14 as shown in FIG. 3. The chassis 16 and one or more extensions 24 may then be proximally retracted as a unit such that each of the extensions 24 slide axially through a respective perforation in the wall 34 of the distal end 26 of the endoluminal prosthesis 12 and the endoluminal prosthesis 12 is allowed to fully deploy and engage the inside surface 78 of the body lumen 14 of the patient as shown in FIG. 4.

Figure 11:
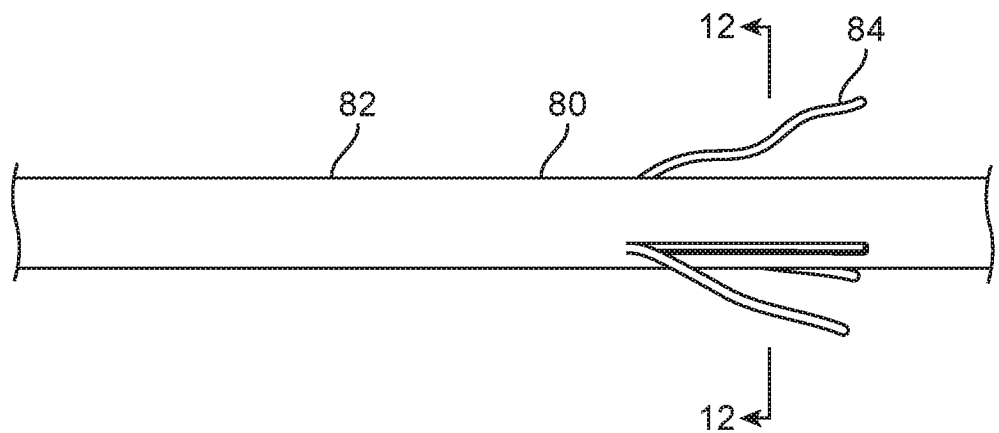
FIG. 11 is an elevation view of a section of an elongate chassis and extensions extending therefrom wherein the extensions have been cut from a tubular structure of the elongate chassis.
Figure 12:
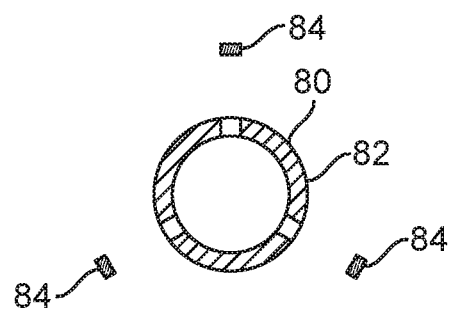
FIG. 12 is a transverse cross section of the elongate chassis and extensions of FIG. 11 taken along lines 12-12 of FIG. 11.
Figure 13:
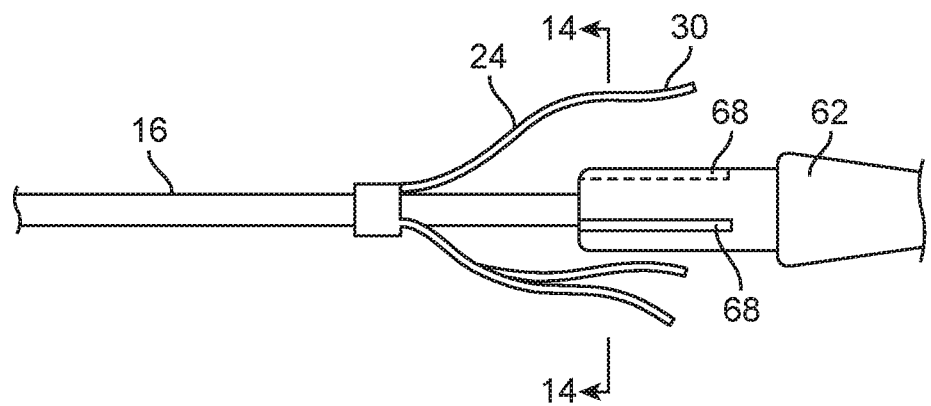
FIG. 13 is an elevation view of the elongate chassis, extensions and nosecone of a catheter system embodiment.
Figure 14:
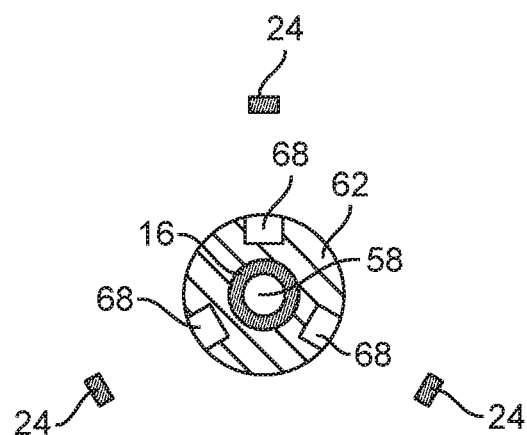
FIG. 14 is a transverse cross section of the elongate chassis and extensions of FIG. 13 taken along lines 14-14 of FIG. 13.
Figure 15:
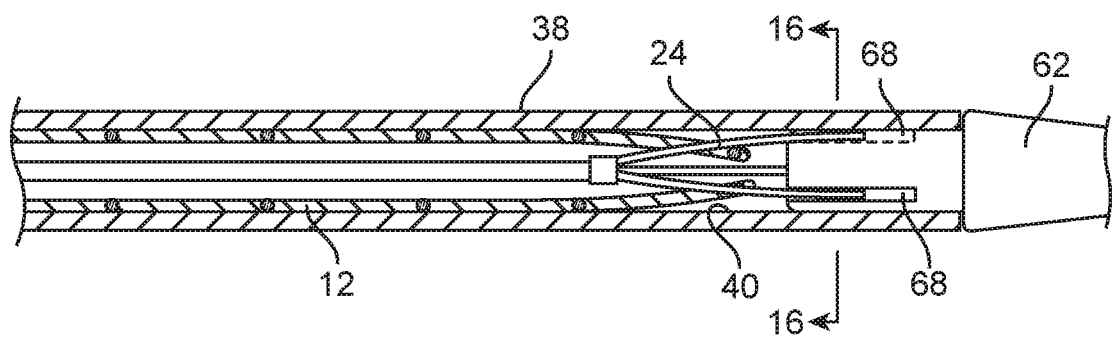
FIG. 15 is an elevation view of partial section of a distal portion of a catheter system embodiment.
Figure 16:
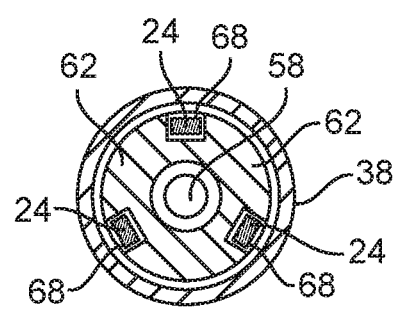
FIG. 16 is a transverse cross section of the outer sheath, nosecone and extensions of the catheter system of FIG. 15 taken along lines 16-16 of FIG. 15.

Referring to FIGS. 11 and 12, an embodiment of an elongate chassis 80 that may be used in any suitable catheter system embodiment 10 discussed herein is shown that includes a tubular member 82 of flexible, resilient material that has a plurality extensions 84 configured for endoluminal prosthesis retention cut directly from the tubular member 82 of the elongate chassis 80. Such an "as cut" configuration of the elongate chassis 80 may be made from any suitable high strength resilient materials such as stainless steel, and shape memory materials such as nickel titanium alloy and the like. For shape memory embodiments, the extensions 84 may be heat set into any of the shapes and configurations as discussed above with regard to the other extension embodiments including the same or similar length, cross section area, s-shape configuration angle formed with respect to the longitudinal axis 42 of the chassis 16, 80 etc. The extensions 84 may be cut from the tubular chassis 80 by any suitable method including laser cutting, water jet cutting, wire EDM or the like.

Figure 17:
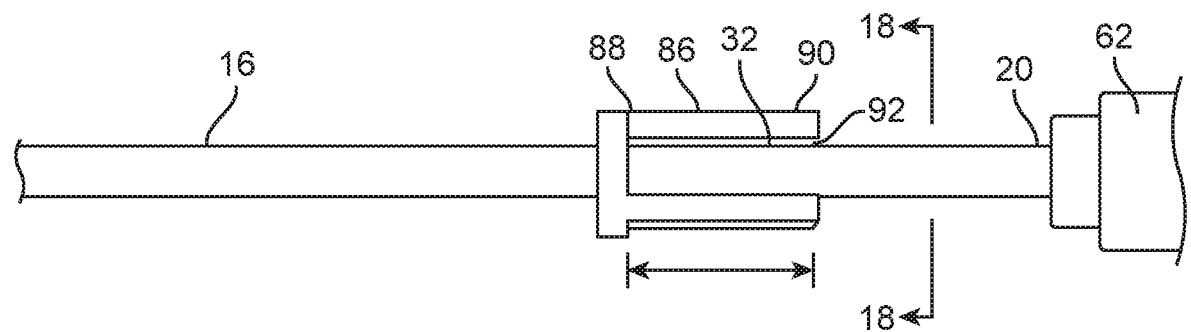
FIG. 17 is an elevation view of an elongate chassis, extensions and nosecone of a catheter system embodiment.
Figure 18:
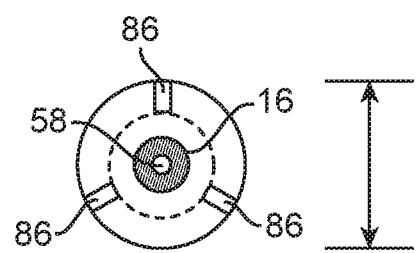
FIG. 18 is a transverse cross section of the elongate chassis of the catheter system of FIG. 17 taken along lines 18-18 of FIG. 17.

Referring to FIGS. 17 and 18, an embodiment of an elongate chassis 16 including substantially rigid extensions 86 configured for endoluminal prosthesis retention for use in catheter system embodiments 10 for deploying an endoluminal prosthesis 12 in a body lumen 14 of a patient is shown. The elongate chassis 16 may have one or more such rigid extension embodiments 86 secured in a fixed relation thereto. The rigid extension embodiments 86 may include a proximal end 88 which is secured in fixed relation to the elongate catheter chassis 16 and a distal end 90 which is disposed radially outward from an outside surface 32 of the chassis 16 and distal of the proximal end 88 of the extension 86. Such substantially rigid extension embodiments 86 may extend through a respective perforation in the wall 34 of a distal end 26 of the endoluminal prosthesis 12 such that the extensions 86 at least partially capture the distal segment 36 of the endoluminal prosthesis 12 and restrict proximal displacement of the endoluminal prosthesis 12 relative to the chassis 16. In this sense, the rigid extensions 86 may function similarly to the extensions 24 discussed above. The term substantially rigid used in this context herein is meant to include extensions 86 the distal ends 90 of which are not deflected or displaced during normal use by an amount more than about 1 mm with respect to the chassis 16 due to forces imposed by the endoluminal prosthesis 12 on the extensions 86 during deployment of the endovascular graft 12. The extension embodiments 86 may otherwise have the same or similar lengths as the lengths discussed above with regard to the flexible resilient extension embodiments 24. The distal ends 90 of the substantially rigid extensions 86 may be disposed with a gap 92 between distal ends 90 of the extensions 86 and the outside surface 32 of the chassis 16 of about 0.5 mm to about 5 mm. The substantially rigid extensions 86 may be made from any suitable high strength material or materials including metal and metal alloys such as stainless steel, nickel titanium, composite materials or the like.

Referring to FIGS. 19-22, a catheter system embodiment 100 for deploying an endoluminal prosthesis 12 in a body lumen 14 of a patient is shown. The catheter system includes the flexible elongate chassis 16 having a proximal end 18, a distal end 20, a distal section 22 and an overall column strength sufficient for advancement of the chassis through a body lumen 14 of a patient. Such a catheter system 100 may also include a self-expanding tubular endoluminal prosthesis 12 disposed in a constrained state over the distal section 22 of the chassis 16. In addition, the catheter system 100 may include one or more thin, flexible, axial belts 102 with each axial belt 102 having a fixed end 104 which is secured in fixed relation to the elongate catheter chassis 16 and a free end 106 which is disposed opposite the fixed end 104. For such catheter system embodiments, each axial belt 102 may form a loop 108 that extends proximally from the fixed end 104 and free end 106 through a distal segment 36 of a wall 34 of the endoluminal prosthesis 12. The free end 106 of each axial belt 102 may be releasably secured in fixed relation to the chassis 16 with a circumferential belt 110 which is disposed about the chassis 16 and free ends 106. The circumferential belt 110 may be configured to apply an inward radial force on the free end 106 of each axial belt 102 sufficient to releasably secure each free end 106 in fixed relation to the chassis 16. The inward radial force of the circumferential belt may be generated by tension of circumferential belt 110 squeezing the free ends 106 against the outside surface 32 of the chassis 16. In such a fixed relation, the loop is configured to capture the distal segments 36 of the endoluminal prosthesis 12 around which the loops 108 are disposed so as to restrict proximal displacement of the endoluminal prosthesis 12 relative to the chassis 16.

For some such embodiments, the circumferential belt 110 may be releasably secured around the free ends 106 and chassis 16 in a tensioned state by a trigger wire 112 which passes through looped ends 118 of the circumferential belt 110. Such a trigger wire 112 may extend axially along or within the chassis 16 from the circumferential belt 110 to the proximal end 18 of the chassis 16 and ultimately to a deployment handle 114 of a proximal adapter 116. The deployment handle 114 may be actuated so as to apply axial translation of the trigger wire 112 in a proximal direction and retract the trigger wire from the end loops 118. In some cases, it may be desirable for the trigger wire 112 to have sufficient stiffness in order to keep end loops 118 of the circumferential belt 110 in fixed relation to each other until the trigger wire 112 is withdrawn while still maintaining sufficient flexibility to be advanced through tortuous body lumens 14 of the patient. Some trigger wire embodiments 112 may be made from high strength resilient flexible materials including metals and metal alloys such as nickel titanium alloy including superelastic nickel titanium alloy as well as stainless steel, composite materials and the like. In some cases, the trigger wire 112 may have a cross section area of about 0.002 mm$^2$ to about 0.06 mm$^2$, more specifically, about 0.04 mm$^2$ to about 0.05 mm$^2$.

For those catheter system embodiments that include a plurality of axial belts 102, the plurality of axial belts 102 may be evenly distributed about the chassis 16 with respect to circumferential orientation about the chassis 16. For some embodiments, the one or more axial belts 102 may have a length of about 10 mm to about 25 mm. For some embodiments, each of the one or more axial belts 102 may have a transverse cross section area of about 0.002 mm$^2$ to about 0.16 mm$^2$, more specifically, about 0.05 mm$^2$ to about 0.09 mm$^2$. In some cases, the catheter system 100 may include 1 axial belt 102 to 10 axial belts 102, more specifically, 2 axial belts 102 to 6 axial belts 102 and even more specifically, 3 axial belts 102 to 4 axial belts 102. In some cases, the axial belt 102 and releasable circumferential belt 110 may be made from any suitable high tensile flexible material including solid wires or braided or stranded filaments of metals including metal alloys such as stainless steel, superelastic nickel titanium as well as solid, braided or stranded filaments of high strength polymers such as nylon, aramid fibers and the like.

In some cases, a respective distal segment 36 of the endoluminal prosthesis 12 may be captured by the loop 108 of each of the one or more axial belts 102. Each distal segment 36 may include the high strength stent element 54 of the self-expanding stent 56 of the endoluminal prosthesis 12. In addition, the stent element 54 captured by each of the loops of the one or more axial belts 102 may include a crown section of the stent 56 (not shown). The high strength stent element 54 may include a resilient and optionally superelastic material such as nickel titanium alloy or the like.

For some embodiments, the chassis 16 may optionally include a guidewire lumen 58 extending from the proximal end 18 of the chassis 16 to the distal end 20 of the chassis 16. In some instances, the catheter system 100 may also include a nosecone 62 secured to the distal end 20 of the chassis 16. The nosecone may have a shoulder portion 64 which is disposed within a distal end 66 of the tubular outer sheath 38. The optional tubular outer sheath 38 which is disposed over the endoluminal prosthesis 12 and chassis 16 may include an inner surface 40 that at least partially radially constrains the endoluminal prosthesis 12 in the constrained state.

Figure 10:
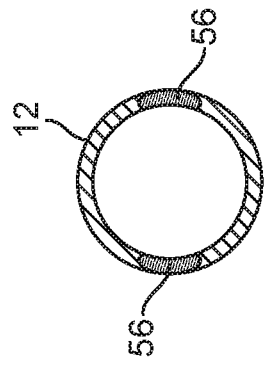
FIG. 10 is a transverse cross section of the endoluminal prosthesis embodiment of FIG. 9 taken along lines 10-10 of FIG. 9.

In some cases, the tubular endoluminal prosthesis embodiments 12 discussed herein may be a tubular stent graft including at least one layer of thin, compliant material 70 secured to the self-expanding stent 56 as shown in FIGS. 9 and 10. For some of these embodiments, the thin compliant material 70 may include nylon mesh, PTFE, ePTFE or the like. In some instances, the stent graft 12 may be a fully stented stent graft as shown in FIG. 9 wherein the helical resilient and undulating stent 56 which is secured to the tubular graft material 70 extends all the way from a distal end 26 of the stent graft 12 to a proximal end 72 of the stent graft 12.

Figure 23:
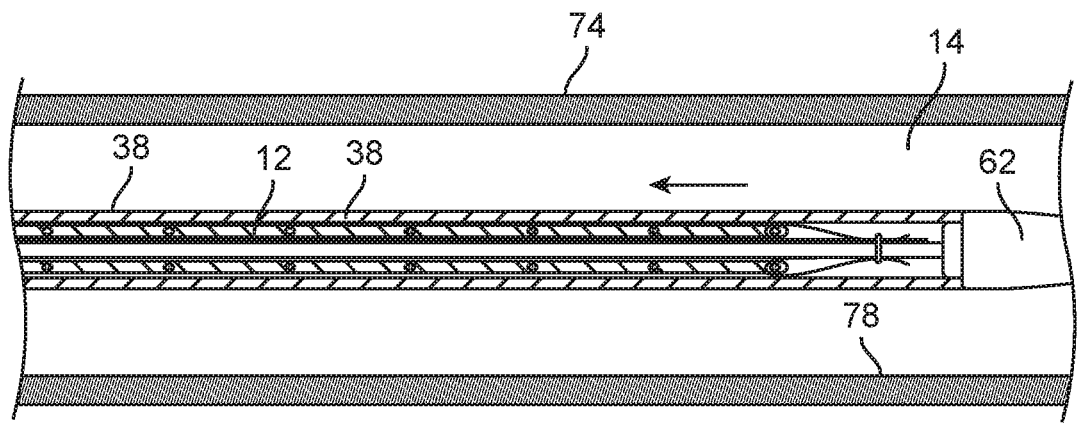
FIG. 23 is an elevation view in partial section of the catheter system of FIG. 19 disposed within a patient's body lumen.
Figure 24:
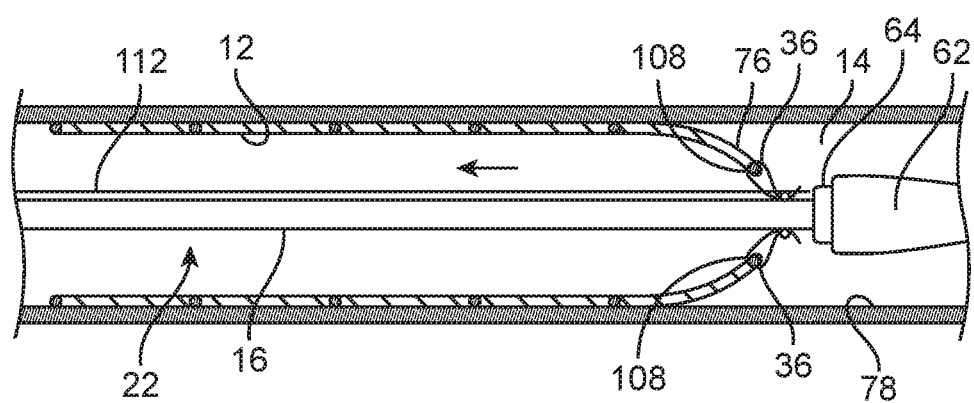
FIG. 24 is an elevation view in partial section of the catheter system of FIG. 19 disposed within a patient's body lumen with an outer sheath proximally retracted and the endoluminal prosthesis of the catheter system partially deployed within the patient's body lumen.
Figure 25:
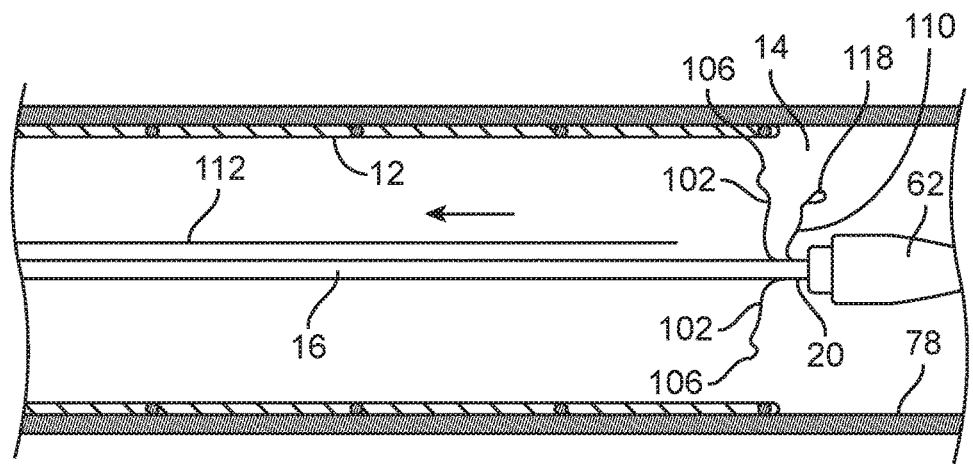
FIG. 25 is an elevation view in partial section of the catheter system of FIG. 19 disposed within a patient's body lumen with the endoluminal prosthesis fully deployed and engaging the patient's body lumen.

In use, referring to FIGS. 23-25, a method for deploying the endoluminal prosthesis 12 in the body lumen 14 of a patient may include advancing the catheter system 100 into the body lumen 14 of the patient until the endoluminal prosthesis 12 of the catheter system is disposed at a treatment site 74 as shown in FIG. 23. In some cases, it may be desirable to advance the catheter system 100 to the treatment site 74 over the guidewire 60 which may be previously disposed across a treatment site 74, which may be moved along ahead of the catheter system 100 in a step by step approach or by any other suitable method. An outer constraint, such as the outer sheath 38, may be removed from the endoluminal prosthesis 12 while the axial belts 102 restrict proximal axial movement of the endoluminal prosthesis 12 relative to the chassis as shown in FIG. 24. Removal of the outer constraint on the endoluminal prosthesis 12 may include proximal retraction of the outer sheath 38 as indicated by arrow 120 in FIG. 23. In some cases, the outer sheath 38 may be proximally retracted by applying proximal tension to the retraction handle 67 relative to the chassis 16. As discussed above, the axial belts 102 may include the fixed end 104 which is secured in fixed relation to the elongate catheter chassis 16 and the free end 106 which is disposed opposite the fixed end 104. The axial belts 102 form the loops 108 that extend proximally from the fixed ends 104 and free ends 106 through the distal segment 36 of the wall 34 of the endoluminal prosthesis 12. The free ends 106 of the axial belts 102 are releasably secured in fixed relation to the chassis 16 with the circumferential belt 110 which is disposed about the chassis 16 and free ends 106. The loops 108 of each of the one or more axial belts 102 capture and restrict axial movement in a proximal direction of the respective distal segments 36 of the endoluminal prosthesis 12. The endoluminal prosthesis 12 may be allowed to self-expand by removal of the constraint, such as by proximal retraction of an outer sheath 38, such that an outside surface 76 of the endoluminal prosthesis 12 contacts an inside surface 78 of the patient's body lumen 14. The tension of the circumferential belt 110 and resulting inward radial force may then be released from the one or more axial belts 102 by proximal retraction of the trigger wire 112 from the end loops 118 of the circumferential belt 110. The free ends 106 of the axial belts 102 are thereby released from the distal segments 36 of the endoluminal prosthesis 12. In this way, the endoluminal prosthesis 12 is allowed to further self-expand and be fully deployed and engage the inside surface 78 of the body lumen 14. The chassis 16 and one or more axial belts 102 may then be proximally retracted such that the axial belts 102 are withdrawn from respective perforations in the wall 34 of the distal end of the endoluminal prosthesis 12 as shown in FIG. 25.

Figure 26:
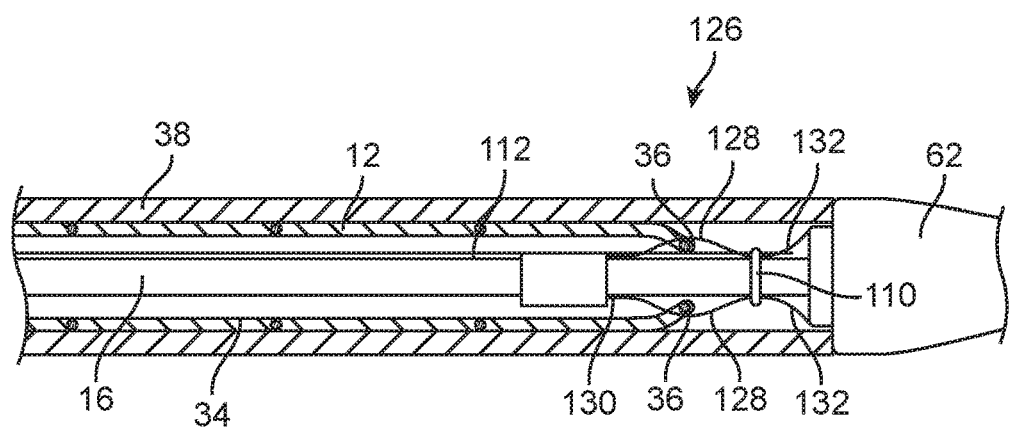
FIG. 26 is an elevation view in partial section of a distal portion of a catheter system embodiment for delivery of an endoluminal prosthesis in a body lumen of a patient.

Referring to FIG. 26, another embodiment of a catheter system 126 is shown which has an endoluminal prosthesis restraint system which is similar to that of the catheter system 100 of FIGS. 19-22. However, instead of each loop 108 of each axial belt 102 extending from the fixed end 104 around the distal segment 36 and back to the free end 106, as is the case with catheter system 100 of FIGS. 19-25, the axial belts 128 of the catheter system embodiment 126 of FIG. 26 extend distally from a fixed end 130 which is secured to the chassis 16, through a respective perforation in the wall 34, around a distal segment 36 of the endovascular prosthesis 12 and then to a free end 132. The free ends 132 may be similarly releasably secured in fixed relation to the chassis 16 with a circumferential belt 110 and trigger wire 112 arrangement with the same or similar arrangement to that of the catheter system embodiment 100 of FIGS. 19-22 with the same or similar features, dimensions and materials.

Figure 27:
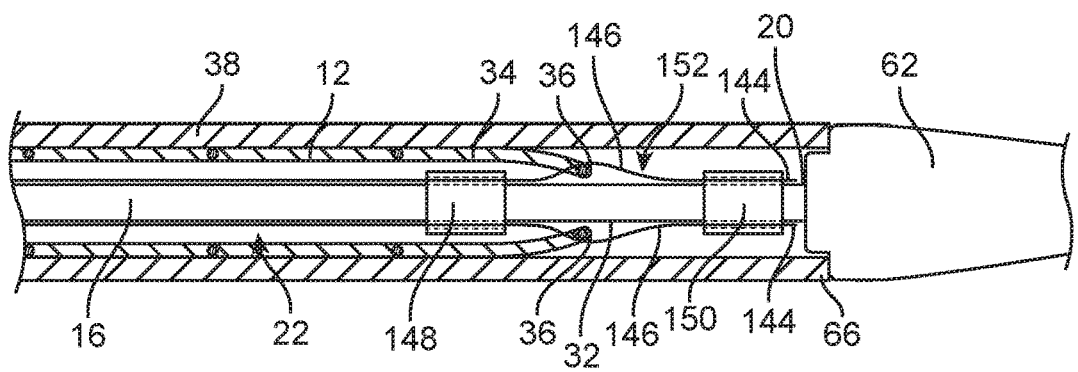
FIG. 27 is an elevation view in partial section of a distal portion of a catheter system embodiment for delivery of an endoluminal prosthesis in a body lumen of a patient.
Figure 28:
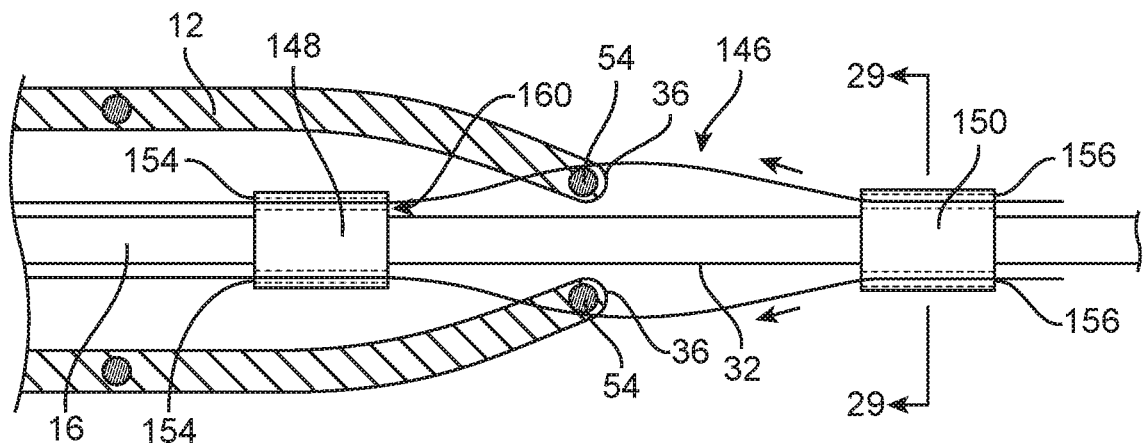
FIG. 28 is an enlarged view of the distal portion of the catheter system of FIG. 27.
Figure 29:
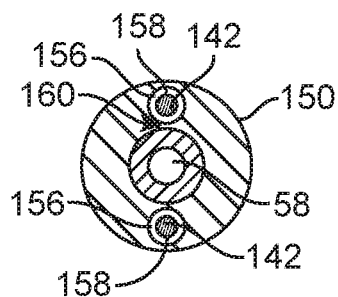
FIG. 29 is a transverse cross section of the elongate chassis of the catheter system of FIG. 28 taken along lines 29-29 of FIG. 28.

Referring to FIGS. 27-29, a catheter system 140 for deploying an endoluminal prosthesis in a body lumen of a patient includes a flexible elongate chassis 16 having a proximal end 18, a distal end 20, a distal section 22 and an overall column strength sufficient for advancement of the chassis 16 through a body lumen 14 of a patient. Such a catheter system 140 may also include a self-expanding tubular endoluminal prosthesis 12 disposed in a constrained state over the distal section 22 of the chassis 16. In addition, the catheter system 140 may include a plurality of axial release wires 142, with each axial release wire 142 having a proximal end, a distal end 144 and a distal section 146. The distal section 146 of each release wire 142 may extend through a distal segment 36 of a wall 34 of the endoluminal prosthesis 12 with the distal section 146 releasably secured in fixed relation to a pair of axially spaced bushings, including a proximal most bushing 148 and a distal most bushing 150. The bushings 148, 150 are secured to and extend radially outward from the chassis 16. Such a structure may be configured so as to form a loop structure 152 having a continuous enclosed structure formed between the distal section 146, the axially spaced bushings 148, 150 and an outside surface 32 of the chassis 16, such that this loop structure 152 releasably captures s respective distal segment 36 of the endoluminal prosthesis 12 and restricts proximal displacement of the endoluminal prosthesis 12 relative to the chassis 16. This configuration may also restrict outward radial displacement of the distal segments 36 which are captured by the respective loop structures 152.

For some embodiments, the release wires 142 may be releasably secured to the spaced bushings 148, 152 in a configuration wherein the release wires 142 are disposed through a longitudinal lumen 154 of the proximal most bushing 148 and a corresponding longitudinal lumen 156 of the distal most bushing 150. In some cases, it may be desirable for the longitudinal lumens 154, 156 of the bushings 148, 150 to have an inner diameter with a substantially close fit to an outside surface 158 of the release wire 142 disposed therein. In these cases, the substantially close fit of the longitudinal lumens 154, 156 may provide additional radial support and stability to the release wire 142 disposed therein. In some cases, corresponding longitudinal lumens 154, 156 of the proximal most bushing 148 and distal most bushing 150 may be coaxial or otherwise aligned with each other. In some cases, the spacing and configuration of the bushings 148, 150 and longitudinal lumens 154, 156 may be important for the performance of the catheter system 140. For some embodiments, the spaced bushings 148, 150 may have an axial length of about 2 mm to about 15 mm, more specifically, about 5 mm to about 10 mm and an outer diameter of about 2 mm to about 6 mm, more specifically, about 2 mm to about 3.5 mm. A longitudinal gap between a distal end of the proximal most bushing 148 and a proximal end of the distal most bushing 150 may be about 4 mm to about 16 mm and a gap 160 between the longitudinal lumens 154, 156 of the spaced bushings 148, 150 and outside surface 32 of the chassis 16 may be about 0.5 mm to about 5 mm in some cases.

For some embodiments, the plurality of axial release wires 142 may be evenly distributed with respect to circumferential orientation about the chassis 16 and spaced bushings 148, 150. Such release wires 142 may extend axially along or within the chassis 16 from the spaced bushings 148, 150 to the proximal end 18 of the chassis 16 and be coupled to a deployment handle, such as deployment handle 114 disposed on a proximal adapter 116 shown in FIG. 19. In some cases, it may be desirable for the release wires 142 to have sufficient stiffness in order to keep distal segments 36 of the endoluminal prosthesis 12 in fixed relation to the chassis 16 until the release wires 142 are withdrawn by proximal retraction from the handle 114 disposed at a proximal adapter 116 of the catheter system 140. However, the release wires 142 should still maintain sufficient flexibility to be advanced through tortuous body lumens 14 of the patient. Some release wire embodiments 142 may be made from high strength resilient flexible materials including metals and metal alloys such as nickel titanium alloy including superelastic nickel titanium alloy as well as stainless steel, composite materials and the like. In some cases, the release wires 142 may have a cross section area of about 0.04 mm$^2$ to about 0.06 mm$^2$. In some cases, the catheter system 140 may have 2 axial release wires 142 to 10 axial release wires 142, more specifically, 2 axial release wires 142 to 6 axial release wires 142, and even more specifically, having 3 axial release wires 142 to 4 axial release wires 142.

In some cases, the respective distal segments 36 of the endoluminal prosthesis 12 captured by the release wires 142 may include a high strength stent element 54 of a self-expanding stent 56 of the endoluminal prosthesis 12. In addition, the stent element 54 captured by each of the release wires 142 may include a crown section of the stent 56. A high strength stent element 54 may include a resilient and optionally superelastic material such as nickel titanium alloy or the like.

For some embodiments, the chassis 16 may optionally include a guidewire lumen 58 extending from the proximal end 18 of the chassis 16 to the distal end 20 of the chassis 16. In some instances, the catheter system 140 may also include a nosecone 62 secured to the distal end 20 of the chassis 16, the nosecone 62 including a shoulder portion 64 which may be disposed within a distal end 66 of a tubular outer sheath 38. An inner surface 40 of the optional outer sheath 38 may be disposed over the endoluminal prosthesis and chassis and at least partially radially constrain the endoluminal prosthesis in the constrained state.

In some cases, the tubular endoluminal prosthesis 12 may be a tubular stent graft including at least one layer of thin, compliant material 70 secured to the self-expanding stent 56. For some of these embodiments, the thin compliant material 70 may include nylon mesh, PTFE, ePTFE or the like. In some instances, the stent graft 12 may be a fully stented stent graft as shown in FIG. 9 wherein the helical resilient and undulating stent 56 which is secured to the tubular graft material 70 extends all the way from the distal end 26 of the stent graft 12 to the proximal end 72 of the stent graft 12.

Figure 19:
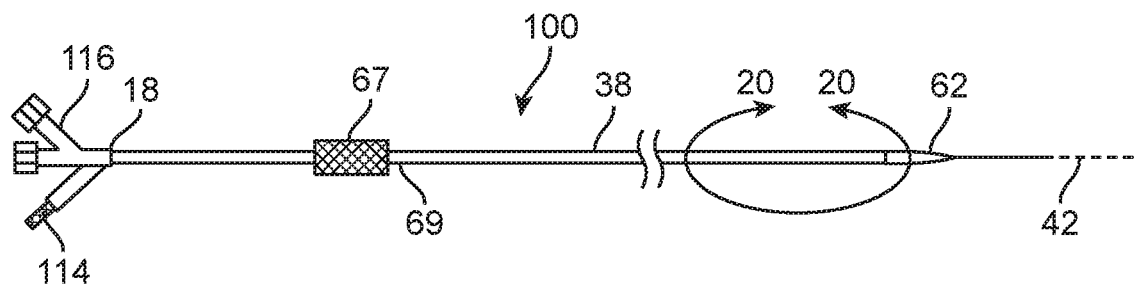
FIG. 19 is an elevation view of a catheter system for deploying an endoluminal prosthesis in a body lumen of a patient.
Figure 20:
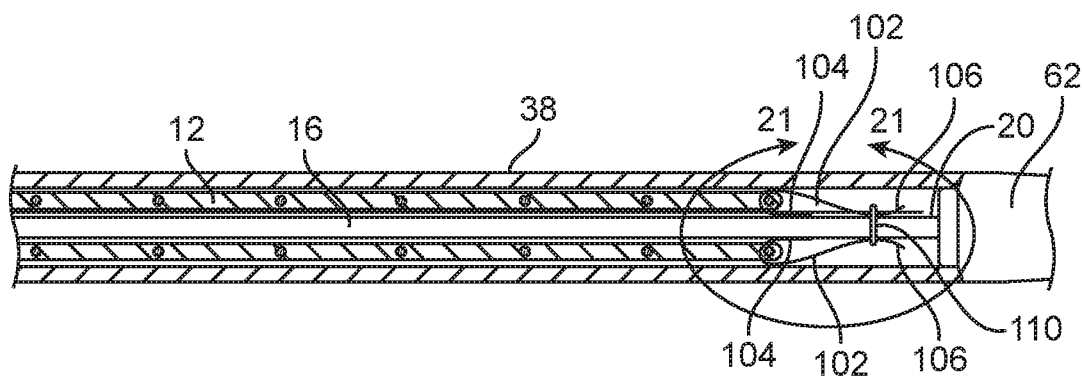
FIG. 20 is an enlarged view in partial section of the catheter system indicated by the encircled portion 20-20 of FIG. 19.
Figure 21:
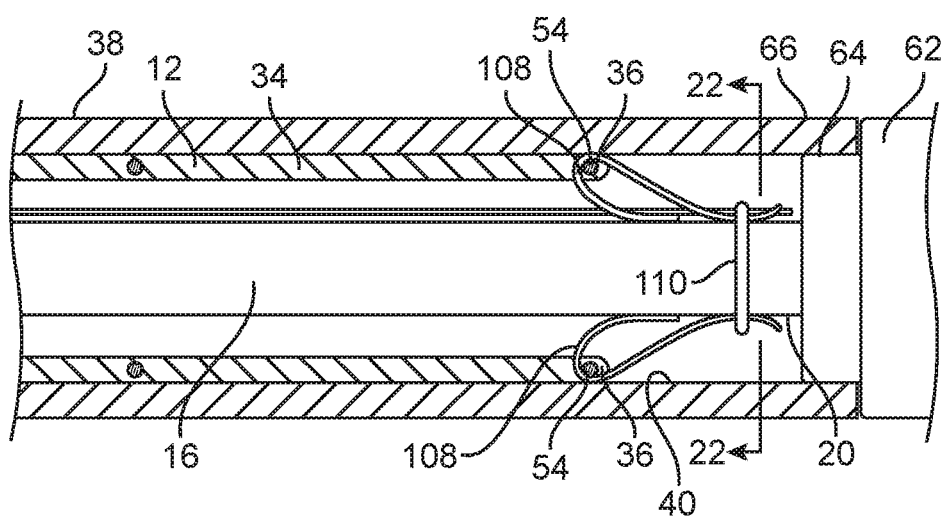
FIG. 21 is an enlarged view in partial section of the catheter system indicated by the encircled portion 21-21 of FIG. 20.
Figure 22:
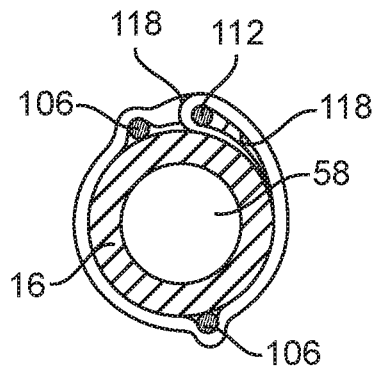
FIG. 22 is a transverse cross section of the catheter system of FIG. 21 taken along lines 22-22 of FIG. 21.
Figure 30:
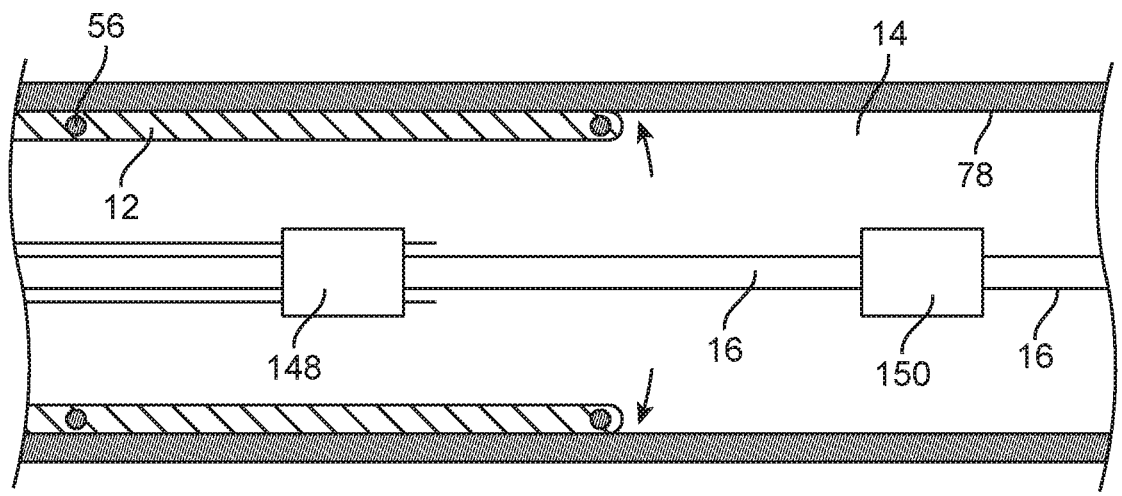
FIG. 30 is an elevation view of the catheter system of FIG. 27 disposed within a body lumen of a patient and the endoluminal prosthesis of the catheter system deployed and engaged with an inner surface of the body lumen.

In use, as shown in FIGS. 28 and 30, deployment of the endoluminal prosthesis 12 may begin with proximal retraction of the optional outer sheath 38 by applying axial tension to the retraction handle 67 which is secured to the proximal end 69 of the outer sheath 38 as shown in FIG. 19. During proximal retraction of the outer sheath 38, proximal displacement of the endoluminal prosthesis 12 is restricted by the loop structures 152 which mechanically capture respective distal segments 36 of the endoluminal prosthesis 12. As discussed above, a proximal axial force may be generated on the endoluminal prosthesis during retraction of the outer sheath 38 due to frictional engagement between the outer surface 76 of the endoluminal prosthesis 12 and the inner surface 40 of the outer sheath 38. The frictional engagement may be due to the outward radial force of the radially constrained self-expanding stent 56 of some embodiments of the endoluminal prosthesis pushing the outside surface 76 against the inner surface 40 of the outer sheath 38.

Once the outer sheath 38 has been proximally retracted, the release wires 142 may then be proximally retracted from the respective longitudinal lumens 154, 156 of the spaced bushings 148, 150, or at least the longitudinal lumens 156 of the distal most bushing 150 as shown in FIG. 28 may be carried out. Once the release wires 142 have been disengaged from at least the distal most bushing 150 and distal segments 36 of the endoluminal prosthesis 12, the endoluminal prosthesis 12 will be allowed to self-expand and engage an inside surface 78 of the body lumen 14 of the patient as shown in FIG. 30. Prior to proximal retraction of the release wires 142, the loop 152 formed between the release wires 142, spaced bushings 148, 150 and outside surface 32 of the chassis 16 serves to restrict axial movement in a proximal direction of the endoluminal prosthesis 12 due to frictional forces imposed on the endoluminal prosthesis 12 by proximal retraction of the optional outer sheath 38 at the initiation of the deployment process. In this way, the axial position of the endoluminal prosthesis 12 is maintained relative to the chassis 16 and body lumen 14 during the deployment process.

Referring to FIGS. 31-41, some embodiments of a catheter system 170 for deploying an endoluminal prosthesis 12 in a body lumen 14 of a patient may include an optional flexible elongate chassis 16 having a proximal end 18, a distal end 20, a distal section 22, a longitudinal axis 42, and a column strength configured for advancement of the chassis 16 through a body lumen 14 of a patient. Such a catheter system 170 may also include a self-expanding tubular endoluminal prosthesis 12 disposed in a constrained state at a distal section 22 of the chassis 16. The catheter system includes a tubular everting sheath 172 which has an inner section 174. The inner section includes a first diameter, a fixed end 176 which is secured in fixed relation to the chassis 16 and an endoluminal prosthesis section 178 that is disposed over and radially constrains the endoluminal prosthesis 12 in the constrained state. The fixed end 176 may be disposed at the distal end of the inner section and in some cases, the inner section 174 may be secured in fixed relation to the chassis 16 at a position that is adjacent a proximal end of the endoluminal prosthesis section 178. The endoluminal prosthesis section 178 is generally disposed at a distal end of the inner section 174 opposite the fixed end 176 and adjacent the distal section 22 of the chassis 16. The inner section 174 joins an outer section 180 at a transition point where there may optionally be a transition in the diameter, thickness and/or material of the everting sheath 172. A first diameter of the inner section 174 is indicated by arrows 179 shown in FIG. 38.

The tubular everting sheath 172 includes also the outer section 180 that is everted back over the endoluminal prosthesis section 178 of the inner section 174 and may also be everted back over some or all of the remainder of the inner section 174 that is proximal of the endoluminal prosthesis section 178. The outer section 180 may include a retraction end 182 and a second diameter which is larger than the first diameter of the inner section 174 such that the outer section 180 is readily slideable over the inner section 174 during retraction of the retraction end 182 and eversion of the everting sheath 172. The retraction end 182 is secured to a retraction handle 186 that may be used to apply proximal axial tension to the outer section 180 relative to the chassis 16 and inner section 174 in order to pull the outer section 180 back over the inner section 174 to evert the everting sheath 172. As such, it may be desirable in some cases for the optional chassis 16 to have sufficient column strength to resist the axial tension applied to the retraction end 182 of the outer section 180 during eversion of the everting sheath 172. The second diameter of the outer section 180 is indicated by arrows 181 shown in FIG. 38.

Figure 35:
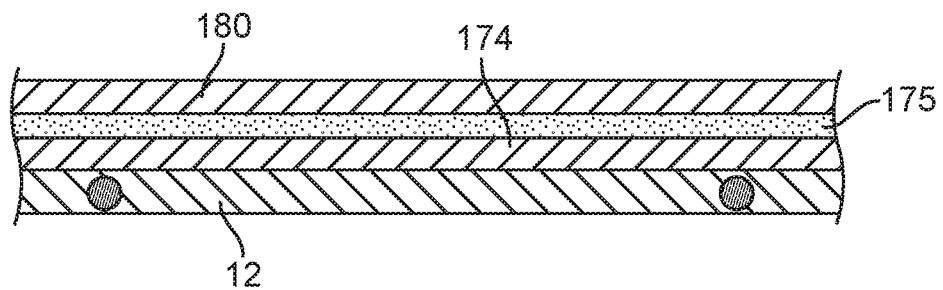
FIG. 35 is an enlarged elevation view in section of a wall portion of the catheter system indicated by the encircled portion 35-35 shown in FIG. 32.
Figure 36:
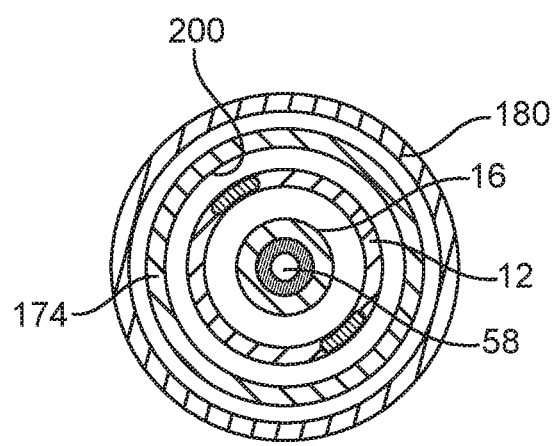
FIG. 36 is a transverse cross section of the catheter system of FIG. 32 taken along lines 36-36 of FIG. 32.
Figure 38:
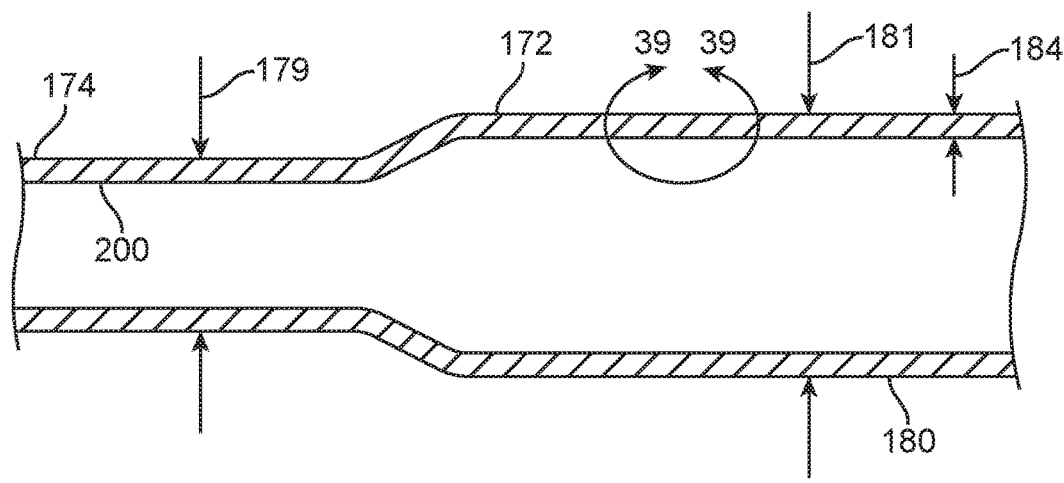
FIG. 38 is an enlarged view of a transition section between an inner section and an outer section of the everting sheath of FIG. 37 as indicated by the encircled portion 38-38 of FIG. 37.

For catheter system embodiments 170 that include the stepped or multi-diameter everting sheath 172, the diameter of the outer section 180 may be greater than the first diameter of the inner section 174 by an amount of at least a wall thickness, indicated by arrows 184 shown in FIG. 38, of the outer section 180 of the tubular everting sheath 172 in some cases. For some embodiments, the thickness 184 of the wall of the everting sheath may be about 0.05 mm to about 2 mm. This dual diameter arrangement may be useful in order to reduce friction and tensile forces on the outer section 180 required to evert the tubular everting sheath 172. For some embodiments, a lubricating material 175 disposed between the inner section 174 and outer section 180 as shown in FIG. 35 may be used to reduce friction between these sections 174, 180 during eversion. Suitable lubricating materials for the lubricating material 175 may include liquids, pastes, gels, including hydrogels as well as tubular structures formed from lubricious materials.

Some embodiments of the everting sheath may also include a PTFE material that has a closed cell microstructure with no distinct fibrils interconnecting adjacent nodes such that the outer section is readily slideable over the inner section due at least in part to the lubricious and supple nature of this type of material. Catheter system embodiments that include an everting sheath having a PTFE material with a closed cell microstructure with no distinct fibrils may also optionally be configured without the dual diameter everting sheath wherein the inner section 174 has a different diameter than the outer section 180. As discussed above, various components of the catheter systems and/or endoluminal prosthesis devices discussed herein may include a type of PTFE material that is produced by a wet stretching method or the like that yields a closed cell microstructure having no distinct fibrils interconnecting adjacent nodes as described in commonly owned U.S. Pat. No. 8,728,372, filed by J. Humphrey et al. on Oct. 29, 2010, titled "PTFE Layers and Methods of Manufacturing", which is hereby incorporated by reference herein in its entirety.

Manufacture of these types of specialized PTFE materials may be carried out by any suitable method. Such PTFE materials may be produced by compounding PTFE resin powder with a lubricant material, stretching agent, or combination thereof, and then extruding that compounded material through an extruder such as a ram extruder. The extrudate may then be calendered in order to thin and mechanically work the extrudate. After calendering, one side or both sides of the calendered PTFE layer are sprayed with an isoparaffin-based stretching agent at a prescribed temperature so that the PTFE film or layer is flooded and fully saturated through the thickness of the PTFE layer. The saturated, calendered PTFE layer may then be stretched in a direction that is substantially orthogonal to the calendering direction by a tentering machine to reduce a thickness of the PTFE layer and form a stretched PTFE layer. The stretched PTFE layer may have a thickness of about 0.00005 inch to about 0.005 inch; specifically, the stretched PTFE layer may have a thickness of about 0.0002 inch to about 0.002 inch. The PTFE layer typically is tentered or stretched at an elevated temperature above the glass transition temperature, specifically, from about 80° F. to about 100° F., more specifically, about 85° F. to about 95° F. Wet tentering with the stretching agent allows the PTFE layer to be thinned without creating substantial porosity and fluid permeability in the stretched PTFE layer. While the stretched PTFE layer will have porosity, its porosity and pore size typically will not be large enough to be permeable to liquids, and often will be small enough to have substantially no fluid permeability. In addition, the stretched PTFE layer embodiment does not have the conventional node and fibril microstructure but instead has a closed cell microstructure in which boundaries of adjacent nodes are directly connected with each other. The fluid-impermeable stretched PTFE film or layer typically may have a density from about 0.5 g/cm$^3$ to about 1.5 g/cm$^3$, but it may have a larger or smaller density for some embodiments. In addition, with regard to all of the methods of processing layers of PTFE discussed above, any of the PTFE layers produced by these methods may also be sintered at any point in the above processes in order to substantially fix the microstructure of the PTFE layer. A typical sintering process may be to expose the PTFE layer to a temperature of about 350° C. to about 380° C. for several minutes; specifically, about 2 minutes to about 5 minutes. The various methods discussed above may be used to produce PTFE layers having a variety of desirable properties. Scanning electron microscope (SEM) images of such materials show a generally closed cell microstructure that is substantially free of the conventional node and fibril microstructure commonly seen in expanded PTFE layers. Embodiments of the PTFE film may have low fluid-permeability, or no or substantially no fluid-permeability. One or more of PTFE layer may be used as a barrier layer to prevent a fluid such as a liquid or gas from permeating or escaping therethrough. At a magnification of 20,000, the microstructure of the stretched PTFE layer resembles a pocked-like structure that includes interconnected high density regions and pockets or pores between some of the high density regions. The PTFE film may be considered to have a closed cell network structure with interconnected strands connecting high density regions in which a high density region grain boundary is directly connected to a grain boundary of an adjacent high density region. Unlike conventional expanded PTFE ("ePTFE") which typically has a substantial node and fibril microstructure that is discernable when viewed at a SEM magnification of 20,000, such a PTFE layer lacks the distinct, parallel fibrils that interconnect adjacent nodes of ePTFE and has no discernable node and fibril microstructure when viewed at a SEM magnification of 20,000. The closed cell microstructure of the PTFE layer provides a layer having low or substantially no fluid permeability that may be used as "a barrier layer" to prevent liquid from passing from one side of the PTFE layer to the opposite side. Though such a PTFE film or layer is configured to have low or substantially no fluid permeability, the PTFE layer nonetheless has a porosity. The PTFE layer typically has an average porosity from about 20% to about 80%, and specifically from about 30% and about 70%. In one embodiment, such a PTFE film has a porosity of about 30% to about 40%. In another embodiment, such a PTFE layer has a porosity of about 60% to about 70%. Porosity as described in these figures is meant to indicate the volume of solid PTFE material as a percentage of the total volume of the PTFE film. An average pore size in the PTFE layer may be less than about 20 microns, and specifically less than about 0.5 micron. In one embodiment, such a PTFE layer has an average pore size of from about 0.01 micron to about 0.5 micron. As can be appreciated, if tissue ingrowth is desired, the PTFE film may have an average pore size of greater than about 6.0 microns. As described below, depending on the desired properties of the resultant PTFE layer, embodiments of methods may be modified so as to vary the average porosity and average pore size of the PTFE film in a continuum from 10 microns to 50 microns down to substantially less than about 0.1 micron. In some cases, such a PTFE layer may have a density from about 0.5 g/cm$^3$ to about 1.5 g/cm$^3$, and specifically from about g/cm$^3$ to about 1.5 g/cm$^3$. While the density of the PTFE film is typically less than a density for a fully densified PTFE layer (e.g., 2.1 g/cm$^3$), if desired, the density of the PTFE layer may be densified to a higher density level so that the density of the PTFE layer is comparable to a fully densified PTFE layer. Such a PTFE film embodiment may have an average thickness that is less than about 0.005 inch, specifically from about 0.00005 inch to about 0.005 inch, and more specifically from about 0.0001 inch to about 0.002 inch.

Figure 39:
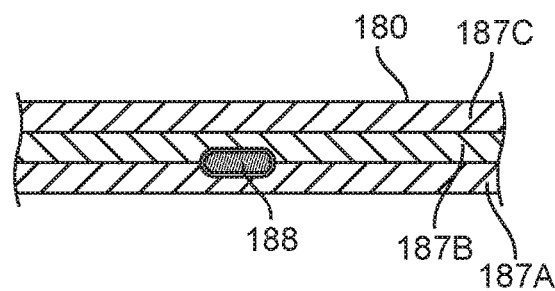
FIG. 39 is an enlarged view of a wall portion of the outer section of the everting sheath of FIG. 38 as indicated by the encircled portion 39-39 of FIG. 38.

In some cases, the everting sheath 172 or sections 174, 180 thereof may include a layered tubular structure including a plurality of layers 187A, 187B, 187C of thin pliable material which are secured together as shown in FIG. 39. In addition, an everting sheath 172 including a single layer of material or any section of an everting sheath formed from a plurality of layers 187 may include for example, any suitable pliable, low friction material such as PTFE, ePTFE, the PTFE having a closed cell microstructure with no distinct fibrils interconnecting adjacent nodes as discussed above or any suitable material.

FIG. 39 illustrates a portion of the outer section 180 of the everting sheath 172 that includes a plurality of layers of material. For the embodiment shown, the everting sheath includes three separate and distinct layers of material that may optionally be fused or bonded together over an entire surface or partial surface of each of the layers 187A, 187B, 187C. Each of the layers may include the same materials or different materials. The number of layers 187 may be varied to achieve desired properties of the everting sheath 172. For some embodiments, the everting sheath may have 1 layer to 10 layers of material, more specifically, 2 layers to 6 layers, and even more specifically, 3 layers to 4 layers of material. In some instances, for everting sheath embodiments 172 that include multiple layers, one or more of the layers may include ePTFE that may or may not be anisotropically oriented and one or more layers of PTFE that has a closed cell microstructure with no distinct fibrils interconnecting adjacent nodes as discussed above.

In some cases, for everting sheath embodiments 172 that include PTFE material and particularly ePTFE material, any of the one or more layers of the everting sheath material may include an anisotropic orientation that provides a greater strength in a first direction relative to a second direction perpendicular to the first direction. For example, a layer of ePTFE material that has an anisotropic orientation providing greater strength in a longitudinal direction may be of particular use for the outer section 180 of the everting sheath 172 which is subjected to longitudinal tensile forces during eversion of the everting sheath 172. For other embodiments, a layer of ePTFE material that has an anisotropic orientation providing greater strength in a circumferential direction may be of particular use for the inner section 174 of the everting sheath 172 which is subjected to outward radial forces of the constrained self-expanding endoluminal prosthesis 12 disposed in the endoluminal prosthesis section 178 of the inner section 174. Any desired combination of these anisotropic materials may be used for the layers of multiple layer everting sheath embodiments 172.

Figure 40:
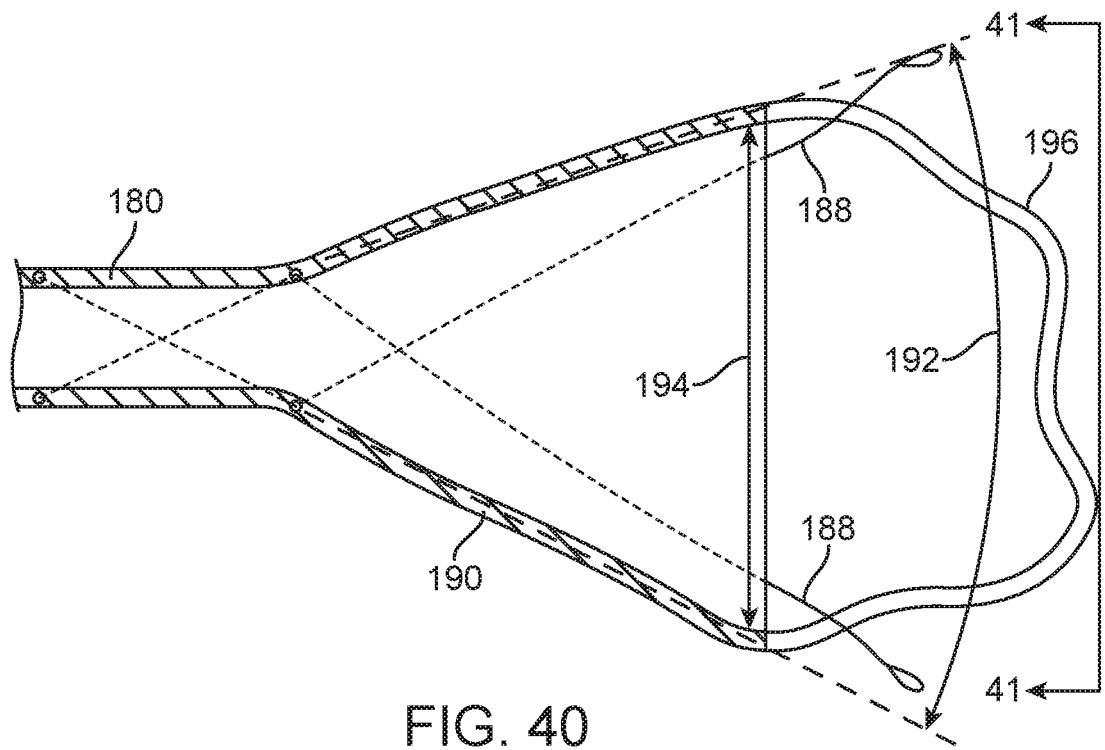
FIG. 40 is an enlarged view of a funnel section disposed at a retraction end of the outer section of the everting sheath of FIG. 37 as indicated by the encircled portion 40-40 of FIG. 37.

For some embodiments of the catheter system 170, any of the everting sheath embodiments 172 may further include one or more thin, elongate, high tensile retraction tethers 188 disposed between adjacent layers 187 of the layered tubular structure of the everting sheath 172 and extending longitudinally along the endoluminal prosthesis section 178 and outer section 180 of the everting sheath 172 as shown in FIGS. 39 and 40. For single layer everting sheath embodiments 172, such retraction tethers 188 may be secured to either surface of the everting sheath. In some cases, the one or more retraction tethers may be helically wound about a tubular structure of the everting sheath 172 as shown in FIG. 40. For the embodiment shown in FIG. 39, the retraction tether 188 is disposed between the first layer 187A and the second layer 187b. The third layer 187C is secured to the second layer 187B. The retraction tether 188 may also be disposed between the second layer 187B and the third layer 187C. For 4 layer everting sheath embodiments (not shown) the retraction tether may be disposed between a first layer and second layer, between the second layer and third layer, or between the third layer and a fourth layer. The retraction tethers 188 may be useful for reinforcing and/or gripping the everting sheath 172 during the eversion process. As such, it may be desirable to secure a retraction end of the retraction tethers 188 to the retraction handle 186.

Figure 37:
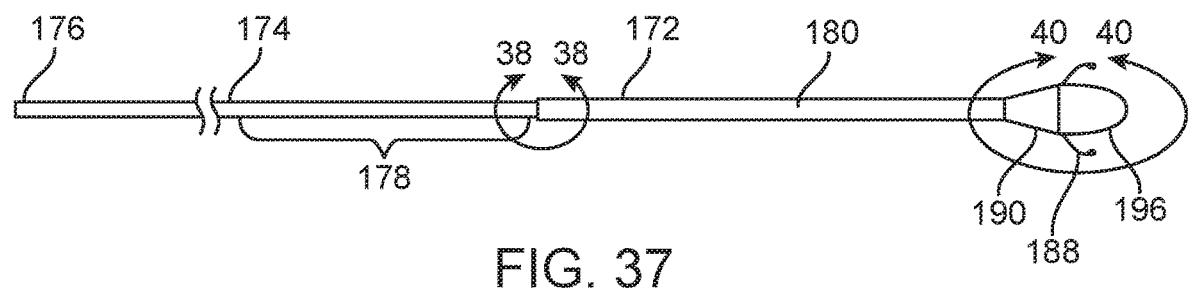
FIG. 37 is an elevation view of an everting sheath embodiment of a catheter system embodiment.
Figure 41:
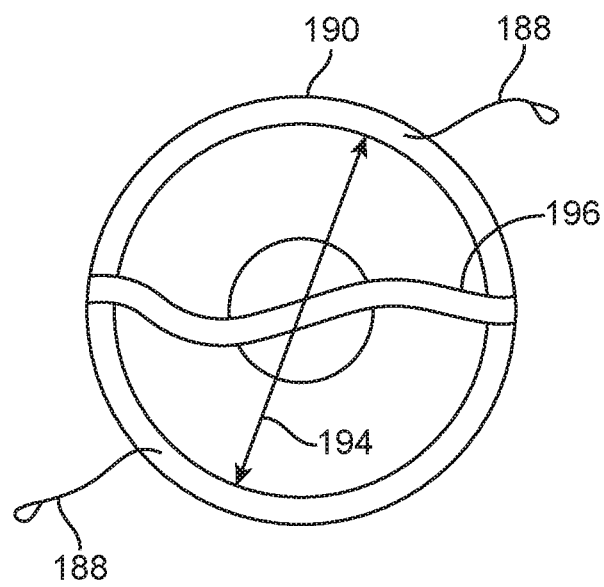
FIG. 41 is an end view of the outer section of the everting sheath of FIG. 37.

In some cases, the everting sheath 172 of the catheter system 170 may include an optional integral funnel section 190 disposed at the retraction end 182 of the outer section 180 of the everting sheath 172 as shown in FIG. 40. The funnel section 190 may be useful for both loading the endoluminal prosthesis 12 into the everting sheath 172 as well as facilitating relative movement between the outer section 180 and inner section 174 during eversion. In some cases, the funnel section 190 may have an inclusive funnel angle as indicated by arrow 192 in FIG. 40, of 10 degrees to 40 degrees. For some embodiments, the funnel section 190 may have a major diameter, indicated by arrow 194 in FIG. 40, at an opening thereof that is greater than an outer diameter of the endoluminal prosthesis 12 in a relaxed expanded state. For some embodiments, an optional integral retraction tether 196 may be secured to and extend from the integral funnel section 190, as shown in FIGS. 37 and 40-41, in order to further facilitate the eversion process and provide an anchor point for the retraction end of the everting sheath 172. As such, the integral retraction tether 196 may be secured to the retraction handle 186.

In some cases, an optional a nosecone 62 may be secured to the distal end 20 of the chassis 16, the nosecone 62 including a shoulder portion 64 which is disposed within a distal end 198 of the tubular everting sheath 172. The nosecone 62 may be secured to the chassis 16 in an axial position which is distal of the endoluminal prosthesis 12 for some embodiments. In some instances, the chassis 16 may include a guidewire lumen 58 extending from the proximal end 18 of the chassis 16 to the distal end 20 of the chassis 16. The chassis 16 may further include an axial length of about 50 cm to about 200 cm for any of the embodiments discussed herein. For the embodiments shown, a proximal adapter 19 is secured to the proximal end 18 of the chassis 16 and is configured to provide an interface for a user of the catheter system 170 for manipulating the proximal end of the catheter system 170 or introducing materials or devices such as guidewires 60 or the like into various lumens of the catheter system 170.

In some cases, the tubular endoluminal prosthesis 12 may be a tubular stent graft including at least one layer of thin, compliant material 70 secured to a self-expanding stent 56. For some of these embodiments, the thin compliant material 70 may include nylon mesh, PTFE, ePTFE or the like. In some instances, the stent graft 12 may be a fully stented stent graft as shown in FIG. 9 wherein the helical resilient and undulating stent 56 which is secured to the tubular graft material 70 extends all the way from a distal end 26 of the stent graft to the proximal end 72 of the stent graft 12.

Figure 42:
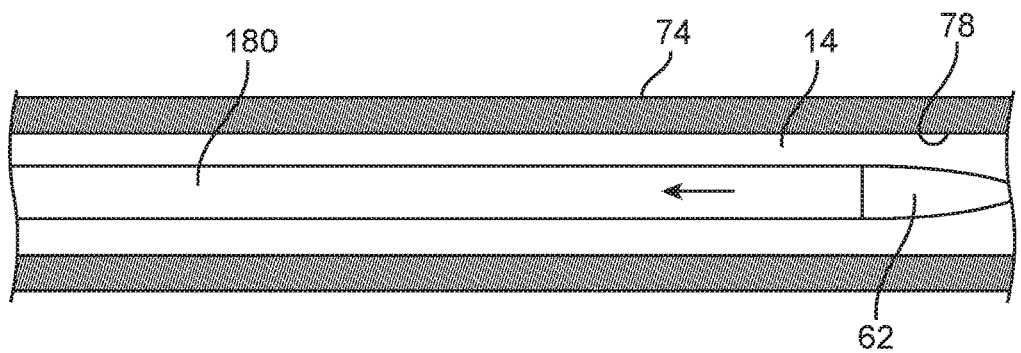
FIG. 42 is an elevation view in partial section showing a distal portion of the catheter system of FIG. 31 disposed within a body lumen of a patient.

In use, referring to FIGS. 42-45, a method for deploying the endoluminal prosthesis 12 in the body lumen 14 of a patient may include advancing the catheter system 170 into the body lumen 14 of the patient until the endoluminal prosthesis 12 of the catheter system 170 is disposed at the treatment site 74 in a constrained state as shown in FIG. 42. In some cases, advancing the catheter system 170 into the body lumen 14 of the patient may include advancing the catheter system over a guidewire 60 until the endoluminal prosthesis 12 of the catheter system is disposed at the treatment site 74 as discussed above in more detail with regard to other catheter system embodiments. The endoluminal prosthesis 12 may be held in the radially constrained state by the inward radial constraint imposed by a substantially non-expandable inside surface 200 the endoluminal prosthesis section 178 of the inner section 174 of the tubular everting sheath 172. This outer constraint on the endoluminal prosthesis 12 may then be fully or partially removed from the endoluminal prosthesis 12 by proximally retracting and displacing the retraction end 182 of the outer section 180 of the tubular everting sheath 172 relative to the chassis 16 and inner section 174 by an eversion process.

Figure 43:
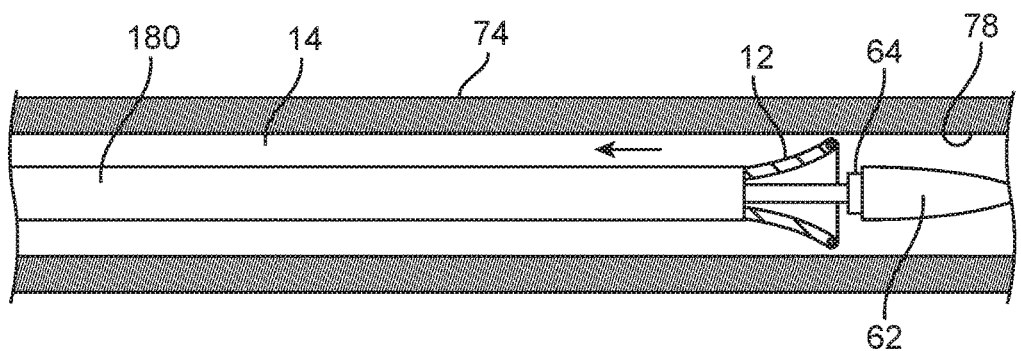
FIG. 43 is an elevation view in partial section showing a distal portion of the catheter system of FIG. 31 disposed within a body lumen of a patient with an everting sheath partially retracted and an endoluminal prosthesis of the catheter system partially deployed.
Figure 44:
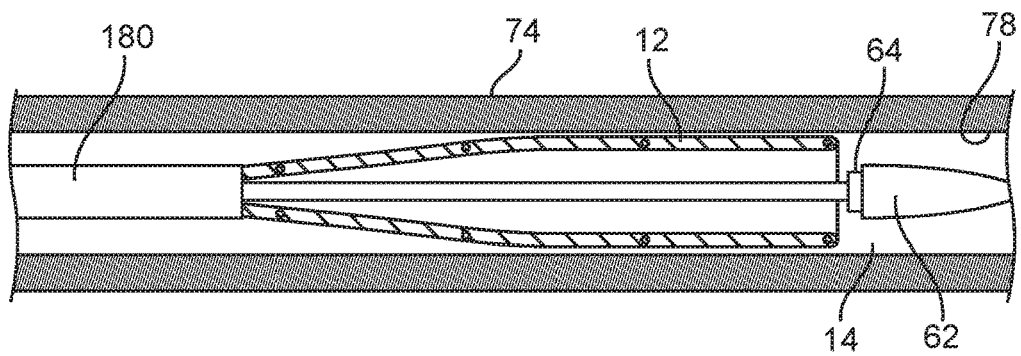
FIG. 44 is an elevation view in partial section showing a distal portion of the catheter system of FIG. 31 disposed within a body lumen of a patient with an everting sheath partially retracted and an endoluminal prosthesis of the catheter system partially deployed.
Figure 45:
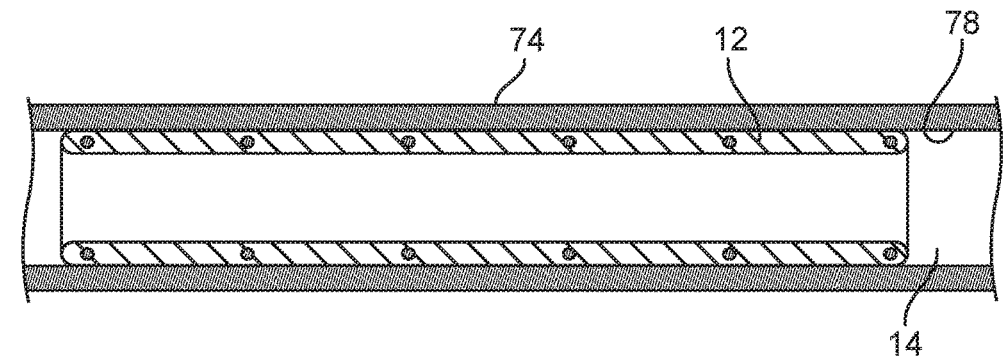
FIG. 45 is an elevation view in section showing the endoluminal prosthesis of the catheter system of FIG. 31 fully deployed and engaging an inside surface of the patient's body lumen.

During the eversion process, the retraction end 182 and outer section 180 of the everting sheath 172 are pulled back proximally relative to the chassis 16 while the inner section 174 remains stationary but peels up at the distal end as it folds back over on itself due to the axial displacement of the outer section 180 connected thereto. This process may be continued until the outer section 180 and distal portion of the inner section 174 are everted proximally back from the endoluminal prosthesis section 178 of the inner section 174 as shown in FIG. 43. That is, eversion is carried out until the endoluminal prosthesis section 178 of the inner section 174 has been peeled back thereby exposing the endoluminal prosthesis and completely removing the inward radial constraint of the endoluminal prosthesis section 178. The endoluminal prosthesis 12 will thus be allowed to self-expand due to this removal of the outer constraint. As the endoluminal prosthesis 12 self-expands, an outside surface 76 of the endoluminal prosthesis 12 may then engage an inside surface 78 of the patient's body lumen 14 as shown in FIG. 44. In most cases, the retraction end 182 of the outer section 180 is proximally retracted until the everting sheath 172 and the constraint imposed by the endoluminal prosthesis section 178 of the everting sheath 172 is completely removed from the endoluminal prosthesis 12.

Figure 46:
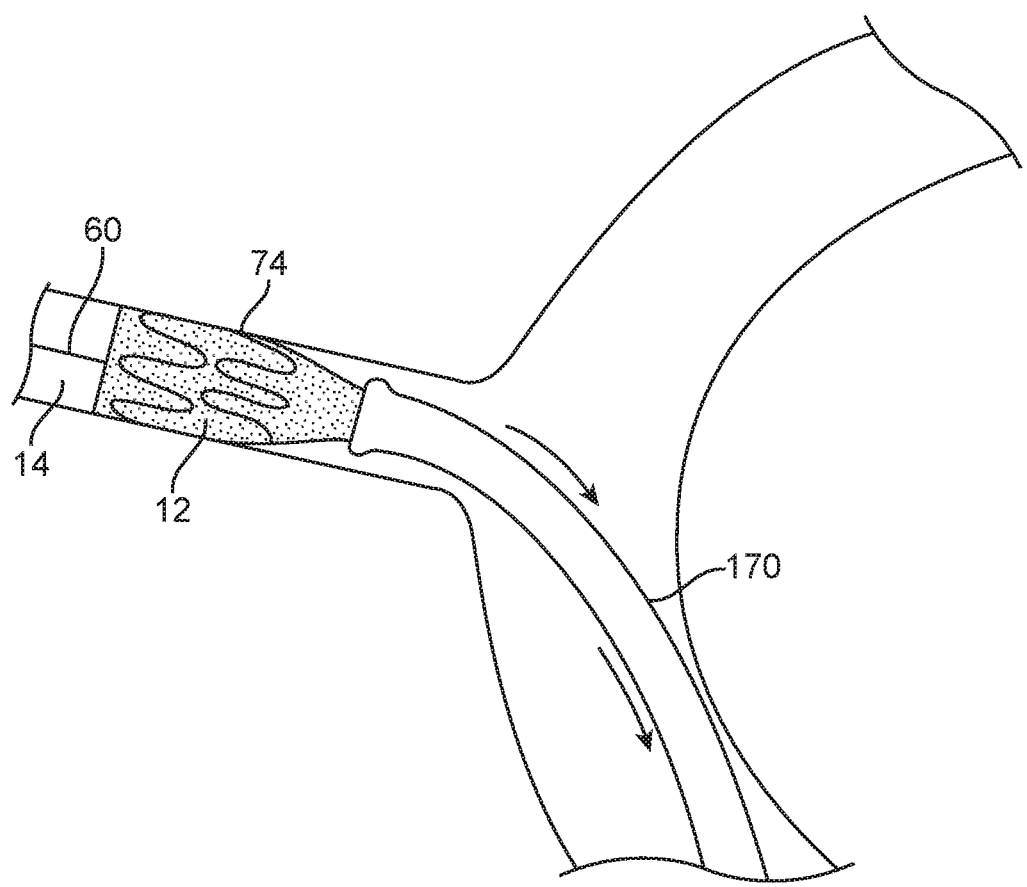
FIG. 46 shows a distal portion of the catheter system of FIG. 31 disposed in an iliac body lumen of a patient.

This method for deploying the endoluminal prosthesis 12 with catheter system 170 may be used to deploy any suitable variety of endoluminal prosthesis to any suitable target sites 74. FIG. 46 shows an endoluminal prosthesis 12 being deployed in an inner lumen 14 of an iliac artery of a patient. The deployment of such an endoluminal prosthesis 12 at such an iliac artery lumen may be carried out by any of the catheter system embodiments and corresponding methods of use discussed herein.

Figure 31:
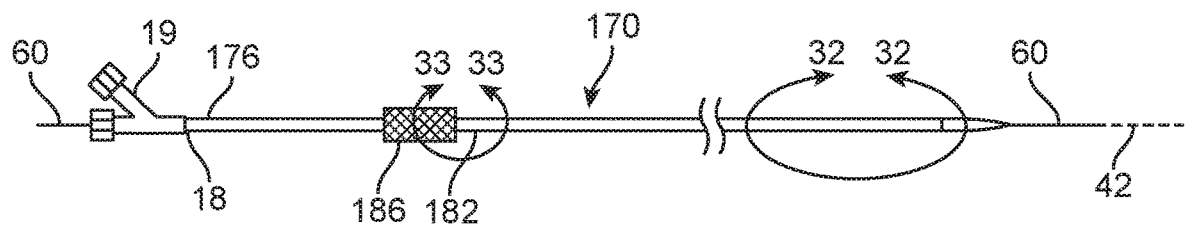
FIG. 31 is an elevation view of a catheter system for deploying an endoluminal prosthesis in a body lumen of a patient.
Figure 32:
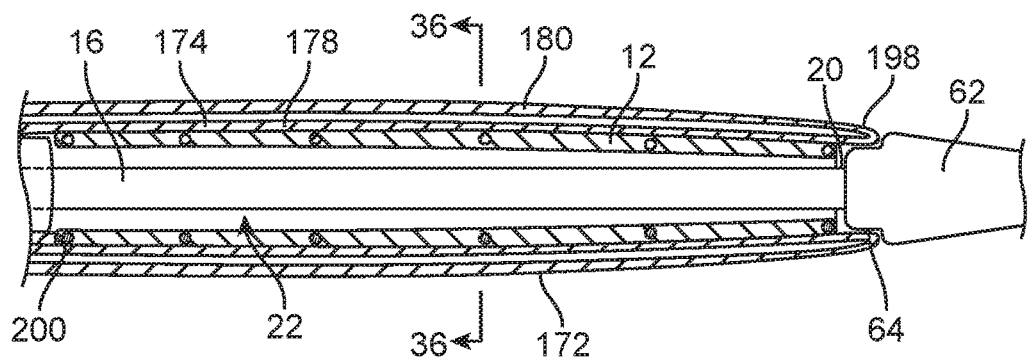
FIG. 32 is an enlarged view in partial section of the catheter system and body lumen indicated by the encircled portion 32-32 of FIG. 31.
Figure 33:
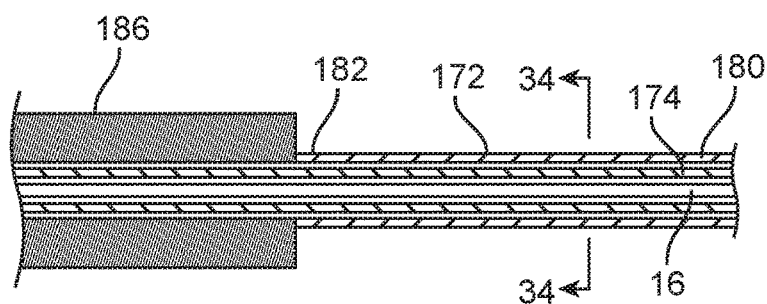
FIG. 33 is an enlarged view in partial section of the catheter system and body lumen indicated by the encircled portion 33-33 of FIG. 31.
Figure 34:
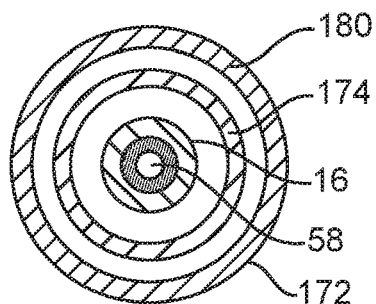
FIG. 34 is a transverse cross section of the catheter system of FIG. 33 taken along lines 34-34 of FIG. 33.
Figure 47:
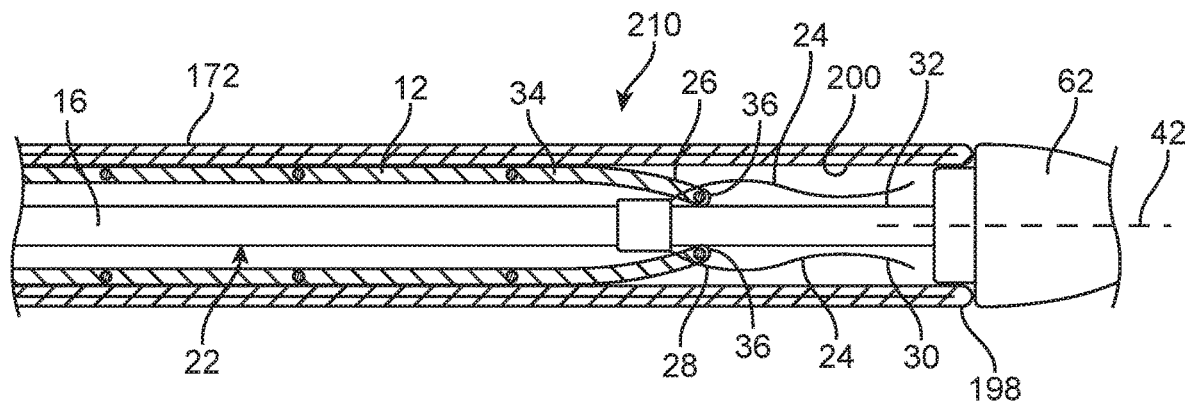
FIG. 47 is an enlarged view in partial section of another embodiment of the catheter system and body lumen indicated by the encircled portion 32-32 of FIG. 31 that includes flexible resilient extensions operatively secured to the chassis and passing through a distal segment of an endoluminal prosthesis embodiment.

In some cases, it may be useful to combine the endoluminal prosthesis retention capabilities of any of the catheter system embodiments 10, 100, 126, 140 discussed above with the everting sheath deployment capabilities of the catheter system 170 or any other everting sheath catheter system discussed herein. In this way, the axial position of the endoluminal prosthesis may be efficiently maintained during eversion of the everting sheath 172. Referring to FIG. 47, some embodiments of a catheter system embodiment 210 may include a flexible elongate chassis 16 having a proximal end 18, a distal end 20, a distal section 22, a longitudinal axis 42, and an overall column strength sufficient for advancement of the chassis 16 through a body lumen 14 of a patient. The catheter system 210 may also include a self-expanding tubular endoluminal prosthesis 12 disposed in a constrained state over the distal section 22 of the chassis 16 and one or more thin, flexible, resilient extensions 24 that extend through a wall 34 of a distal end 26 of the endoluminal prosthesis 12. The extensions 24 may be disposed in a radially constrained state such that each extension 24 at least partially captures a distal segment 36 of the endoluminal prosthesis 12 and restricts proximal displacement of the endoluminal prosthesis 12 relative to the chassis. The extensions 24 may each include a proximal end 28 which is secured in fixed relation to the elongate catheter chassis 16 and a distal end 30 which is disposed radially outward from an outside surface 32 of the chassis 16 and distal of the proximal end 28 of the extension 24. The catheter system 210 includes a tubular everting sheath 172 which has an inner section 174 which includes a fixed end 176 which is secured in fixed relation to the chassis 16 and an endoluminal prosthesis section 178 that is disposed over and radially constrains the endoluminal prosthesis 12 and extensions 24 in the constrained state. The tubular everting outer sheath 172 may also have an outer section 180 that is everted back over the endoluminal prosthesis section 178 of the inner section 174. The outer section also includes a retraction end 182 as shown in FIG. 31 which is disposed at an opposite end of the everting sheath 172 as the fixed end 176. In general, the catheter system 210 may include the same or similar features, dimensions or materials as those of any of the catheter systems discussed herein.

The everting sheath 172 is disposed over the endoluminal prosthesis 12 and chassis 16 and includes an inner surface 200 of the endoluminal prosthesis section 178 that constrains the endoluminal prosthesis in the constrained state. The inner surface 200 also radially constrains the distal ends 30 of the extensions 24 in a radially constrained state as shown in FIG. 47. Such a radially constrained state of the distal ends 30 of the extensions 24 may provide more leverage for the extensions 24 to restrict proximal axial movement of the endoluminal prosthesis 12 because the radial constraint on the distal ends 30 of the extensions 24 prevents them from pivoting in a proximal direction when proximal tension is applied to the endoluminal prosthesis 12. For some embodiments, the extensions 24 may have distal ends 30 that extend radially outward from the chassis in a relaxed unconstrained state by a distance similar to a radius of the endoluminal prosthesis 12 to be deployed when that endoluminal prosthesis 12 is also in an unconstrained state. In some instances, an angle the flexible extensions 24 form with respect to the longitudinal axis 42 of chassis 16 may be 5 degrees to 50 degrees with the extension 24 in a relaxed unconstrained state as shown in FIG. 8. The angle of the flexible extension 24 with respect to the longitudinal axis 42 of the chassis 16 may in some cases be defined by the angle between the longitudinal axis 42 of the chassis 16 and a line extending from the proximal end 28 of the extension 24 to the distal end 30 of the extension 24 as shown in FIG. 8.

Because of the resilience of some extension embodiments 24, the distal ends 30 of these extensions 24 may be easily passed through the wall 34 of the endoluminal prosthesis 12 when both the endoluminal prosthesis 12 and the extension 24 are in a relaxed unconstrained state. Both the endoluminal prosthesis 12 and the extension 24 may be radially constrained by an inward radial force and held in that constrained state by the inner surface 200 of the of the inner section 174 of the everting sheath 172 as shown in FIG. 47. In order to achieve both a proper flexibility and resilience as well as sufficiently strong bending moment in order to resists failing under an axial load from the endoluminal prosthesis 12, some extension embodiments 24 may be made from a resilient high strength material such as a metal alloy or composite material. For some embodiments, the extensions 24 may be made from or include superelastic nickel titanium alloy. For some such embodiments, the extension 24 may include a transverse cross section area of about 0.08 mm$^2$ to about 1 mm$^2$. For some embodiments, the extension 24 may have a length of about 4 mm to about 25 mm. In some cases, the catheter system 210 may include 1 extension 24 to 10 extensions 24, more specifically 2 extensions 24 to 6 extensions 24 and even more specifically 3 extensions 24 to 4 extensions 24.

In some cases, as shown in FIG. 7 and discussed above, the extensions 24 may lie substantially in a same plane as the longitudinal axis 42 of the chassis 16. In some cases, substantially in the same plane includes within a thickness of the extension 24 of lying in the same plane as the longitudinal axis 42 of the chassis 16. For some embodiments, the plurality of extensions 24 is evenly distributed with respect to circumferential orientation about the chassis 16. In some cases, the extension 24 may have an s-shape in the unconstrained relaxed state as shown in more detail in FIG. 8. For the embodiment shown, the proximal most deflection 46 of the s-shape of the extension extends away from the chassis 16 and a distal most deflection 50 of the s-shape of the extension 24 extends towards the chassis 16.

For some embodiments, the distal segment 36 of the endoluminal prosthesis 12 captured by the extension 24 includes a high strength stent element 54 of a self-expanding stent 56 of the endoluminal prosthesis 12 as shown in FIG. 47. In some cases, the stent element 54 captured by the extension 24 includes a crown section of the stent. A high strength stent element 54 may include a resilient and optionally superelastic material such as nickel titanium alloy or the like.

For some embodiments, the chassis 16 may optionally include a guidewire lumen 58 extending from the proximal end 18 of the chassis 16 to the distal end 20 of the chassis 16. In some instances, the catheter system 210 may also include a nosecone 62 secured to a distal end 20 of the chassis 16 in an axial position which is distal of the endoluminal prosthesis 12. The nosecone 62 may also include a shoulder portion 64 which is disposed within a distal end 198 of a tubular everting sheath 172. For some embodiments, the tubular everting sheath 172 may be disposed over the endoluminal prosthesis 12 and chassis 16 and include an inner surface 200 that at least partially radially constrains the endoluminal prosthesis 12 and one or more extensions 24 in the constrained state. For some such embodiments, referring specifically to FIGS. 13-16, the shoulder portion 64 of the nosecone 62 may further optionally include one or more elongate longitudinally oriented slots 68 which are configured to accept the distal end 30 of the corresponding extensions 24 when the extensions 24 are in the radially constrained state. Some embodiments of these longitudinally oriented slots 68 may be disposed so as to be substantially parallel to and lie substantially in the same plane as the longitudinal axis 42 of the chassis 16. The longitudinally oriented slots 68 in the nosecone 62 may be useful in some instances for stabilizing the distal ends 30 of the one or more extensions 24 when disposed in the radially constrained state.

In some cases, the tubular endoluminal prosthesis 12 may be a tubular stent graft including at least one layer of thin, compliant material 70 secured to a self-expanding stent 56. For some of these embodiments, the thin compliant material 70 may include nylon mesh, PTFE, ePTFE or the like. In some instances, the stent graft 12 may be a fully stented stent graft, as shown in FIG. 9 and discussed above, wherein the helical resilient and undulating stent 56 which is secured to the tubular graft material 70 extends all the way from a distal end of the stent graft to a proximal end of the stent graft 12.

For catheter system embodiments 210 that include the stepped or multi-diameter everting sheath 172, as shown in FIGS. 37-39, the diameter of the outer section 180 may be greater than the first diameter of the inner section 174 by an amount of at least a wall thickness 184 of the outer section 180 of the tubular everting sheath 172 in some cases. For some embodiments, the diameter of the outer section 180 may be greater than the diameter of the inner section 174 by an amount equal to 1 wall thickness of the everting sheath 172 to 4 wall thicknesses of the everting sheath 172. For some cases, the diameter of the inner section 174 and outer section 180 may be measured at a center of the wall thickness at diametrically opposed points of the wall of each respective section 174, 180.

The catheter system 210 includes the tubular everting sheath 172 with the inner section 174 which includes a fixed end 176 which is secured in fixed relation to the chassis 16 and the endoluminal prosthesis section 178 that is disposed over and radially constrains the endoluminal prosthesis 12 and one or more extensions 24 in the constrained state. The tubular everting sheath 172 includes the outer section 180 that is everted back over the endoluminal prosthesis section 178 of the inner section 174 as shown in FIG. 47. The outer section 180 of these embodiments may include the retraction end 182 which may optionally be secured to the retraction handle 186 which is disposed at a proximal section of the catheter system 210 and which is axially slidable with respect to the chassis 16. The everting sheath 172 may include a PTFE material having a closed cell microstructure with no distinct fibrils interconnecting adjacent nodes such that the outer section is readily slideable over the inner section. Catheter system embodiments that include an everting sheath including a PTFE material having a closed cell microstructure with no distinct fibrils may be configured with or without the dual diameter everting sheath 172 wherein the inner section 174 has a different diameter than the outer section 180 as discussed in more detail above.

In some cases, the everting sheath 172 or sections 174, 180 thereof may include a layered tubular structure having a plurality of layers of thin pliable material which are secured together as shown in FIG. 39 and discussed above. An everting sheath 172 including a single layer of material or any layer of an everting sheath formed from a plurality of layers may include any suitable pliable, low friction material such as nylon mesh, PTFE, ePTFE, the PTFE having a closed cell microstructure with no distinct fibrils interconnecting adjacent nodes as discussed above or any other suitable material.

In some cases, for everting sheath embodiments 172 that include PTFE material and particularly ePTFE material, the everting sheath material may include an anisotropic orientation that provides a greater strength in a first direction relative to a second direction perpendicular to the first direction. For example, a layer of ePTFE material that has an anisotropic orientation providing greater strength in a longitudinal direction may be of particular use for an outer section 180 of the everting sheath 172 which is subjected to longitudinal tensile forces during eversion of the everting sheath 172. For other embodiments, a layer of ePTFE material that has an anisotropic orientation providing greater strength in a circumferential direction may be of particular use for an inner section 174 of the everting sheath 172 which is subjected to outward radial forces of the constrained self-expanding endoluminal prosthesis 12 disposed in the endoluminal prosthesis section 178 of the inner section 174.

For some embodiments of the catheter system 210, any of the everting sheath embodiments 172 may further include one or more thin, elongate, high tensile retraction tethers 188 disposed between adjacent layers of the layered tubular structure of the everting sheath 172 and extending longitudinally along the endoluminal prosthesis section 178 and outer section 180 of the everting sheath 172 as shown in FIGS. 39 and 40. For single layer everting sheath embodiments 172, such retraction tethers 188 may be secured to either surface of the everting sheath 172. In some cases, the one or more retraction tethers 188 may be helically wound about a tubular structure of the everting sheath 172 as shown in FIG. 40 and discussed above.

In some cases, the everting sheath 172 of the catheter system 210 may include an optional integral funnel section 190 disposed at the retraction end 182 of the outer section 180 of the everting sheath 172 as shown in FIGS. 40 and 41. The funnel section 190 may be useful for both loading an endoluminal prosthesis 12 into the everting sheath 172 as well as facilitating relative movement between the outer section 180 and inner section 174 during eversion. In some cases, the funnel section 190 may have an inclusive funnel angle 192 of 10 degrees to 40 degrees. For some embodiments, the funnel section 190 may have a major diameter at an opening thereof that is greater than an outer diameter of the endoluminal prosthesis 12 to be deployed in a relaxed expanded state. For some embodiments, an optional integral retraction tether 196 may be secured to and extend from the integral funnel section 190, as shown in FIGS. 37 and 40-41, in order to further facilitate the eversion process and provide an anchor point for the retraction end 182 of the everting sheath 172.

The chassis 16 may further include an axial length of 50 cm to 200 cm for some embodiments. For the embodiments discussed herein, a proximal adapter 19 may be secured to the proximal end 18 of the chassis 16 and configured to provide an interface for a user of the catheter system 210 for manipulating the catheter system 210 or introducing materials or devices such as guidewires 60 or the like into various lumens of the catheter system 210.

Figure 48:
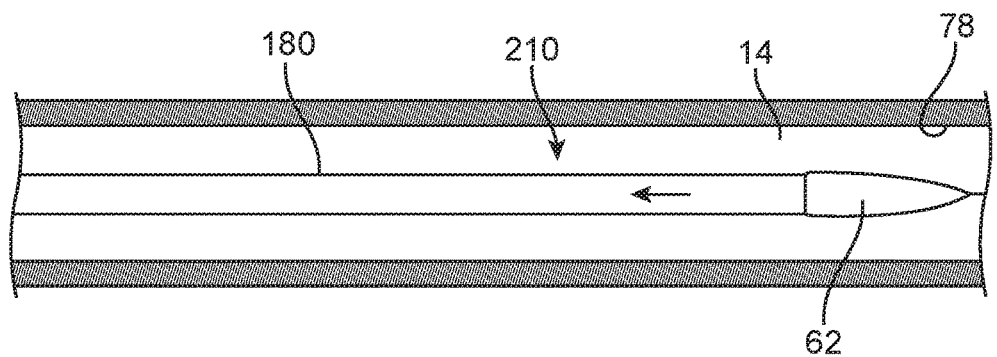
FIG. 48 is an elevation view in partial section showing a distal portion of the catheter system of FIG. 31 disposed within a body lumen of a patient, the catheter system including the optional extensions operatively secured to the chassis as shown in FIG. 47.
Figure 49:
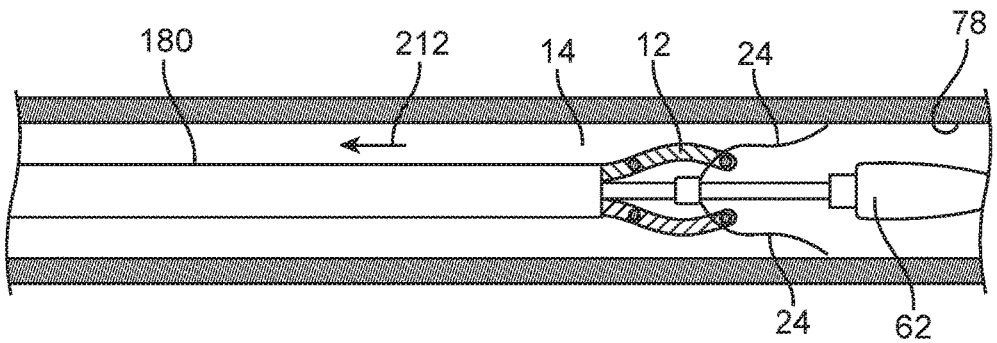
FIG. 49 is an elevation view in partial section showing a distal portion of the catheter system of FIG. 48 disposed within a body lumen of a patient with an everting sheath partially retracted and an endoluminal prosthesis of the catheter system partially deployed.
Figure 50:
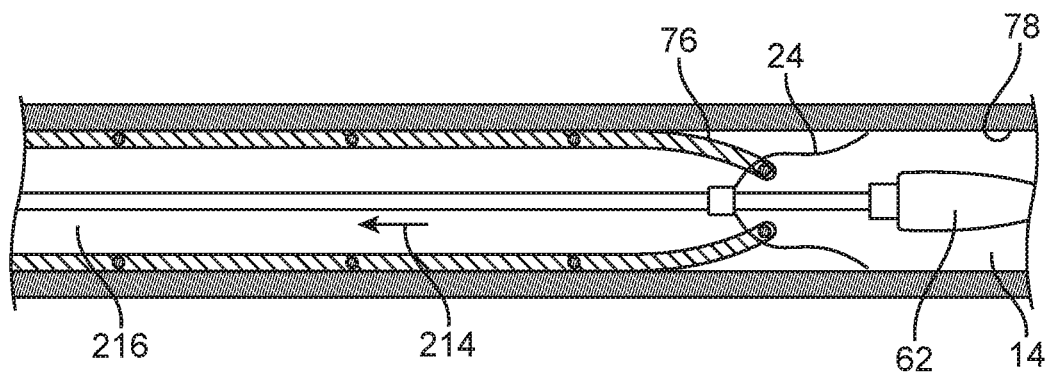
FIG. 50 is an elevation view in partial section showing a distal portion of the catheter system of FIG. 48 disposed within a body lumen of a patient with an everting sheath.

In use, referring to FIGS. 48-52, a method for deploying the endoluminal prosthesis 12 in a body lumen 14 of a patient may include advancing the catheter system 210 for deployment of the endoluminal prosthesis 12 into the body lumen 14 of the patient until the endoluminal prosthesis 12 of the catheter system 210 is disposed at a treatment site 74 as shown in FIG. 48. In some cases, the catheter system 210 may be advanced over the guidewire 60 as shown in FIG. 48. For such a catheter system 210, the endoluminal prosthesis 12 and the resilient, flexible, extension 24 that at least partially captures the distal segment 36 of the endoluminal prosthesis 12 may both be held in a constrained state by the endoluminal prosthesis section 178 of the inner section 174 of the tubular everting sheath 172. The outer constraint may thereafter be removed from the endoluminal prosthesis 12 and the extensions 24 by proximally retracting the retraction end 182 of the outer section 180 of the tubular everting sheath 172 as seen in FIG. 49. Retraction of the outer section 180 may be carried out by the outer section 180 being everted back over the endoluminal prosthesis section 178 of the inner section 174 during the proximal retraction as indicated by the arrow 212 in FIG. 49. This eversion process may be carried out while the extensions 24 prevent proximal axial movement of the endoluminal prosthesis 12 relative to a flexible, elongate chassis 16 of the catheter system 210. In some cases, the outer section 180 is proximally retracted until the everting sheath 172 and constraint imposed by the endoluminal prosthesis section 178 thereof is completely removed from the endoluminal prosthesis 12 and extensions 24 as shown in FIG. 50.

Figure 51:
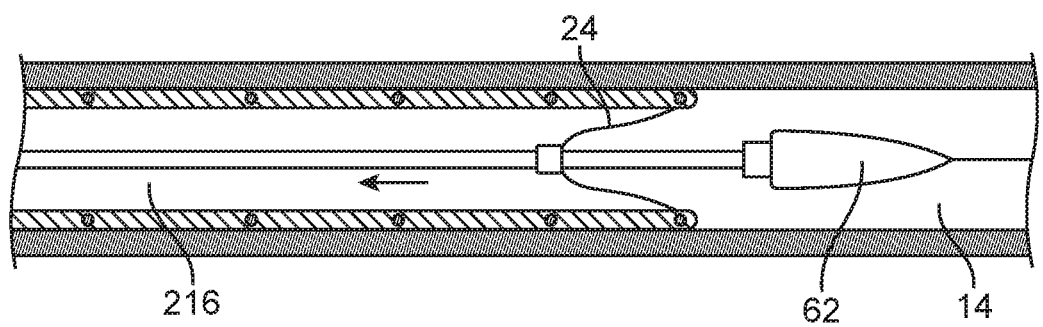
FIG. 51 is an elevation view in partial section showing a distal portion of the catheter system of FIG. 48 disposed within a body lumen of a patient with an everting sheath completely retracted and the optional extensions retracted from the endoluminal prosthesis.
Figure 52:
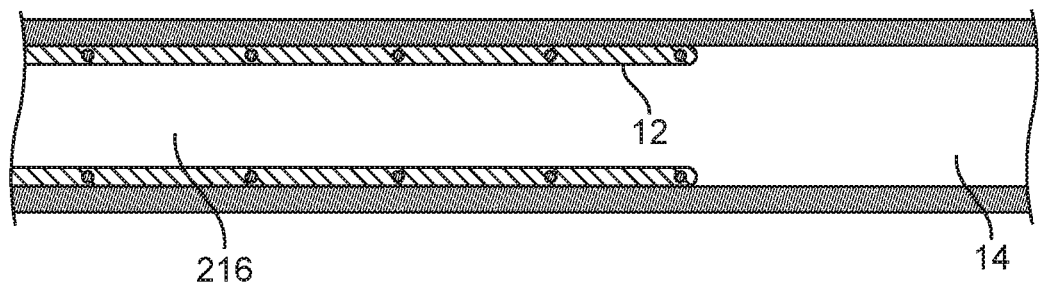
FIG. 52 is an elevation view in section showing the endoluminal prosthesis of the catheter system of FIG. 48 fully deployed and engaging an inside surface of the patient's body lumen.

The endoluminal prosthesis 12 and distal ends 30 of the extensions 24 may thereafter self-expand until an outside surface 76 of the endoluminal prosthesis 12 engages an inside surface 78 of the patient's body lumen 14 as shown in FIG. 50. Finally, the chassis 16 and extensions 24 may be proximally retracted as indicated by arrow 214 in FIG. 50, such that the extensions 24 pass axially through perforations in the wall 34 of the distal end 26 of the endoluminal prosthesis 12 and no longer capture the respective distal segments 36 of the endoluminal prosthesis 12, as shown in FIG. 51. The chassis 16 and extensions 24 may be further proximally retracted until they are no longer disposed within the lumen 216 of the endoluminal prosthesis 12 as shown in FIG. 52.

For the embodiment shown, the proximal end 28 of the extensions 24 are secured in fixed relation to the elongate catheter chassis 16 and the distal ends 30 of the extensions 24 are disposed radially outward from an outside surface 32 of the chassis 16 distal of the proximal ends 28 of the extensions 24 such that allowing the endoluminal prosthesis 12 and extensions 24 to self-expand includes allowing the distal ends 30 of the extensions 24 to pivot outwardly away from the chassis 16.

Figure 53:
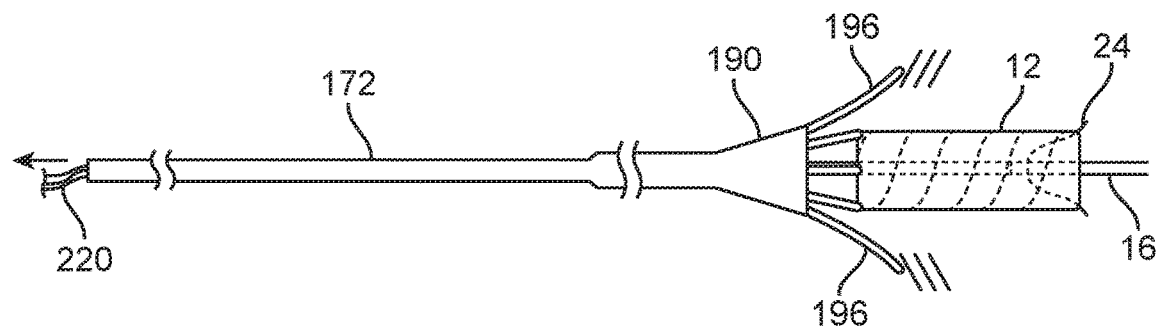
FIG. 53 is an elevation view of an endoluminal prosthesis embodiment and optional elongate catheter chassis being loaded into an everting sheath embodiment.

For some of the catheter system embodiments discussed above, loading a self-expanding endoluminal prosthesis 12, as well as any associated catheter system components such as a chassis 16 etc., into any of the catheter systems discussed herein may be difficult, particularly since large radial and frictional forces may be mutually imposed between the various components of the catheter system. In addition, many of the components of such catheter systems may be fragile or easily damaged when subjected to improper types of forces and contact. As such, it may be desirable to have a suitable method for loading endoluminal prostheses 12 into a catheter system and into a constrained state. Referring to FIGS. 53-58, a method of loading a self-expanding (or any other suitable type) of endoluminal prosthesis 12 into a sheath, such as the everting sheath embodiments 172 discussed above, is shown. The method embodiment shown includes passing a plurality of thin high tensile tether loops 220 through an end of the endoluminal prosthesis 12 as shown in FIG. 53. The plurality of tether loops 220 may also be passed through an inner lumen 222 of the everting sheath 172 also as shown in FIG. 53. In some cases, the tether loops 220 may be made from any suitable high tensile flexible material including solid wires or braided or stranded filaments of metals including metal alloys such as stainless steel, superelastic nickel titanium as well as high strength polymers such as nylon, aramid fibers and the like.

Figure 54:
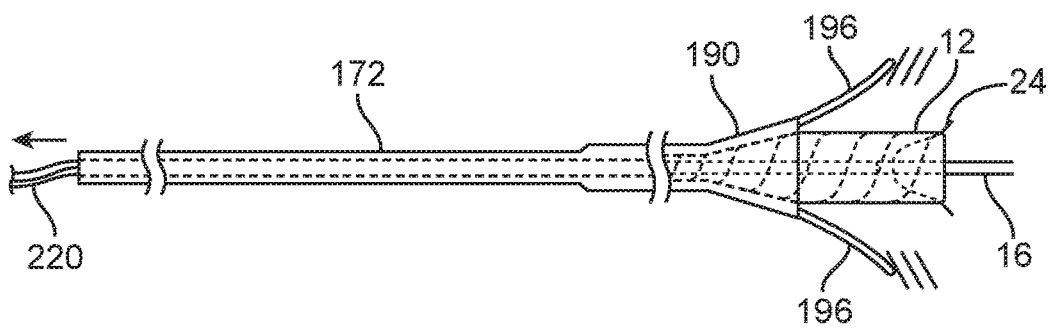
FIG. 54 is an elevation view of the everting sheath embodiment of FIG. 53 with the endoluminal prosthesis and elongate catheter chassis being drawn into the funnel section of the everting sheath such that the endoluminal prosthesis and resilient extensions of the optional chassis are radially constrained.
Figure 55:
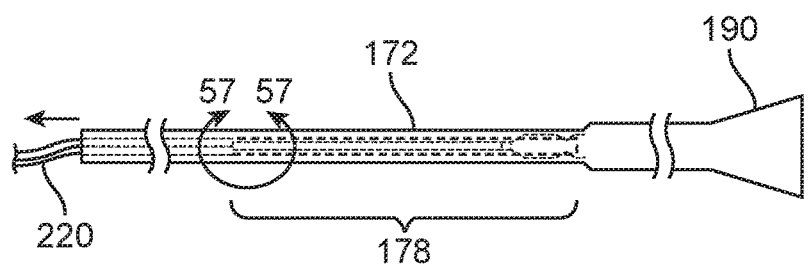
FIG. 55 is an elevation view of the everting sheath of FIG. 53 with the endoluminal prosthesis completely loaded into an endoluminal prosthesis section of the everting sheath.
Figure 56:
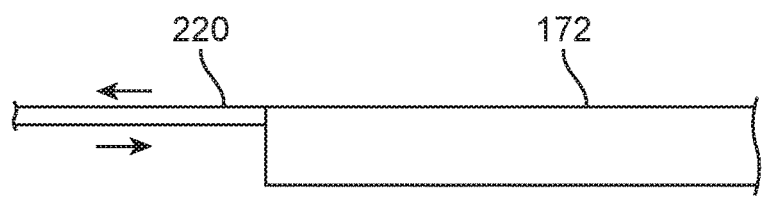
FIG. 56 shows a thin high tensile tether being pulled through the everting sheath and out of an end of the fully loaded endoluminal prosthesis of FIG. 55.
Figure 57:
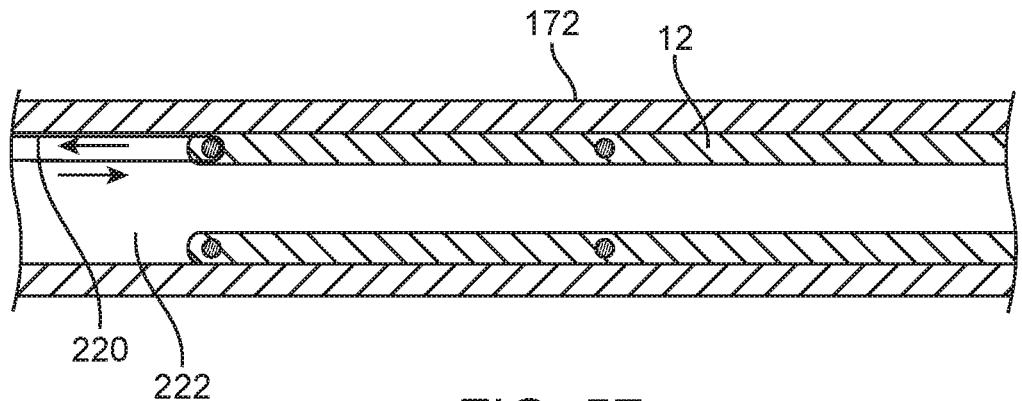
FIG. 57 shows a more detailed view in partial section of the thin high tensile tether being pulled out of an end of the fully loaded endoluminal prosthesis of FIG. 56.
Figure 58:
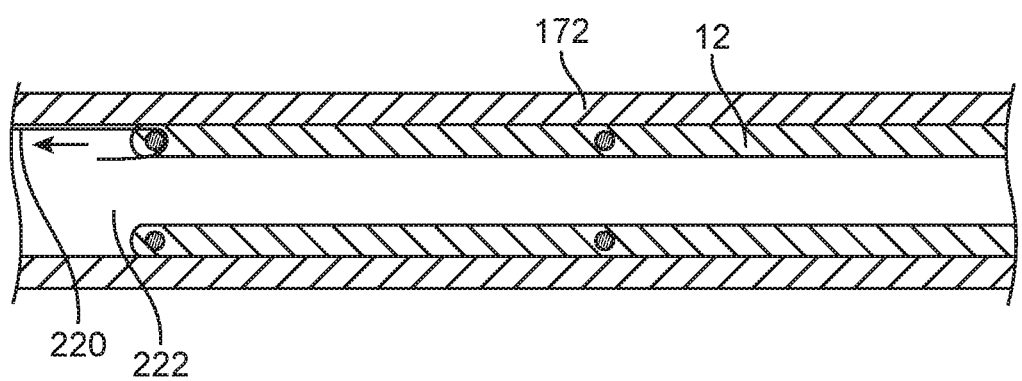
FIG. 58 shows the thin high tensile tether being pulled out of an end of the fully loaded endoluminal prosthesis of FIG. 56.

An end of the everting sheath 172 may be restrained such as by the integral retraction tether 196 of the funnel section 190 as discussed above and shown in FIG. 53 or by any other suitable method. Both ends of each of the tether loops 220 may be pulled on with axial tension being simultaneously applied to both ends of each tether loop 220 in a direction away from the endoluminal prosthesis 12. The axial tension is applied to both ends of each tether loop 220 such that the tether loops 220 are pulled through the inner lumen 222 of the everting sheath 172 and axial tension is thereby applied to the end of the endoluminal prosthesis 12. The axial tension is applied to the endoluminal prosthesis 12 such that the endoluminal prosthesis 12 is thereby pulled into the inner lumen 222 of the everting sheath 172 to an endoluminal prosthesis section 178, or any other desired section, within the inner lumen 222 of the sheath 172 as shown in FIG. 54. As shown in FIG. 53 the endoluminal prosthesis 12 is first pulled into the funnel section 190 prior to entering the inner section 174. The funnel section 190 may be useful for guiding and compressing the endoluminal prosthesis into the inner section 174. Thereafter, by pulling on only one side of each of the tether loops 220 and releasing an opposite end of each tether loop 220, each of the tether loops 220 may slide through and be completely pulled out of the endoluminal prosthesis 12 and the inner lumen 222 of the sheath 178 as shown in FIGS. 56-58.

As shown in FIGS. 53-58, the loading method may also be used to load both an endoluminal prosthesis 12 and a corresponding chassis 16 including flexible resilient extensions 24 extending therefrom. In such instances, the tether loops 220 may be used to pull the endovascular prosthesis, chassis and associated extensions 24 into the inner lumen 222 of the everting sheath 172. As this combined structure is being drawn into the inner lumen 222 due to the axial tension applied to the tether loops 220, both the self-expanding endoluminal prosthesis and distal ends 30 of the extensions 24 will be compressed and radially constrained. The combined structure may be pulled through the inner lumen 222 until the endoluminal prosthesis 12 is disposed at the endoluminal prosthesis section 178 of the inner section 174 or disposed at any other desired location within the inner lumen 222.

As shown in FIGS. 53-58, the sheath being loaded is an everting sheath 172 and pulling the tethers 220 may include pulling the tethers 220 through the everting sheath 172 until the endoluminal prosthesis 12 is disposed within and constrained by an endoluminal prosthesis section 178 of the inner section 174 of such an everting sheath 172. However, such methods may also be used for any other suitable sheath embodiments, including any of the proximally retractable outer sheath embodiments discussed herein that are configured to at least partially constrain a self-expanding endoluminal prosthesis 12, also as discussed above.

The delivery system and method embodiments discussed herein may be particularly useful for endoluminal prosthesis embodiments which include one or more inflatable portions. Such inflatable endoluminal prosthesis embodiments that may be deployed by the systems and methods discussed herein are discussed in U.S. Pat. No. 7,147,660 filed by M. Chobotov et al. on Dec. 20, 2002, titled "Advanced Endovascular Graft" which is hereby incorporated by reference herein in its entirety.

Delivery catheter embodiments discussed herein may include some or all of the features, dimensions or materials of delivery systems discussed in commonly owned U.S. Patent Application Publication No. 2004/0138734, published Jul. 15, 2004, filed Oct. 16, 2003, by Chobotov et al., titled "Delivery System and Method for Bifurcated Graft" and in PCT International Publication No. WO 02/083038, published Oct. 24, 2002, filed Apr. 11, 2001, by Chobotov et al., titled "Delivery System and Method for Bifurcated Graft" each of which is incorporated by reference herein in its entirety.

Endoluminal prosthesis embodiments discussed herein may include some or all of the features, dimensions or materials of the prostheses discussed in commonly owned U.S. Patent Publication No. 2009/0099649, filed Oct. 3, 2008, by Chobotov et al., titled Modular Vascular Graft for Low Profile Percutaneous Delivery, which is incorporated by reference herein in its entirety.

Examples of deployment devices, alignment devices, radiopaque markers delivery methods and the like that may be used in conjunction with any suitable system or component thereof discussed herein may be found in commonly owned U.S. Patent Application No. 2011/0218609, filed Feb. 9, 2011, by M. Chobotov et al., and titled "Fill Tube Manifold and Delivery Methods for Endovascular Graft", and U.S. Patent Publication No. 2013/0268048, filed Mar. 15, 2013, by J. Watson et al., and titled "Delivery Catheter for Endovascular Device", U.S. Patent Publication No. 2013/0268044, filed Mar. 13, 2013, by D. Parsons et al., and titled "Durable Stent Graft with Tapered Struts and Stable Delivery Methods and Devices", each of which is hereby incorporated by reference herein in its entirety.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the embodiments discussed. Although embodiments have been described in substantial detail with reference to one or more specific embodiments, those of ordinary skill in the art will recognize that changes may be made to the embodiments specifically disclosed in this application, yet these modifications and improvements are within the scope and spirit of the disclosure.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

Certain embodiments of the technology are set forth in the claim(s) that follow(s).

What is claimed is:

1. A catheter system for deploying an endoluminal prosthesis in a body lumen of a patient, comprising:
a flexible elongate chassis having a proximal end, a distal end, a distal section and an overall column strength sufficient for advancement of the chassis through a body lumen of a patient;
a self-expanding tubular endoluminal prosthesis disposed in a constrained state over the distal section of the chassis; and
a thin, flexible, resilient extension comprising
a proximal end which is secured in fixed relation to the chassis,
a distal end which is disposed radially outward from an outside surface of the chassis and distal of the proximal end of the extension; and
wherein the extension extends through a wall of a distal end of the endoluminal prosthesis with the extension in a radially constrained state such that the extension at least partially captures a distal segment of the endoluminal prosthesis and restricts proximal displacement of the endoluminal prosthesis relative to the chassis, wherein the extension comprises an s-shape in an unconstrained relaxed state, and wherein a proximal most deflection of the s-shape of the extension extends away from the chassis and a distal most deflection of the s-shape of the extension extends towards the chassis.

2. The catheter system of claim 1 wherein an angle of flexible extension formed with respect to a longitudinal axis of chassis is 5 degrees to 50 degrees with extension in a relaxed unconstrained state.

3. The catheter system of claim 1 wherein the extension comprises a length of 4 mm to 25 mm.

4. The catheter system of claim 1 wherein the extension comprises a transverse cross section area of 0.08 mm$^2$ to 1 mm$^2$.

5. The catheter system of claim 1 comprising a plurality of thin, flexible, resilient extensions, each of the plurality of extensions comprising:
 a proximal end which is secured in fixed relation to the chassis,
 a distal end which is disposed radially outward from an outside surface of the chassis and distal of the proximal end of the extension; and
 wherein each of the plurality of extensions extend through a wall of a distal end of the endoluminal prosthesis with the extensions in a radially constrained state such that each extension at least partially captures a distal segment of the endoluminal prosthesis and restricts proximal displacement of the endoluminal prosthesis relative to the chassis.

6. The catheter system of claim 5 wherein the plurality of extensions are evenly distributed with respect to circumferential orientation about the chassis.

7. The catheter system of claim 5 comprising 2 extensions to 6 extensions.

8. The catheter system of claim 7 comprising 3 extensions.

9. The catheter system of claim 1 wherein the extension lies substantially in a same plane as a longitudinal axis of the chassis.

10. The catheter system of claim 9 wherein a thickness of the extension lies substantially in the same plane as the longitudinal axis of the chassis.

11. The catheter system of claim 1 wherein the distal segment captured by the extension comprises a stent element of a self-expanding stent of the endoluminal prosthesis.

12. The catheter system of claim 11 wherein the stent element captured by the extension comprises a crown section of the stent.

13. The catheter system of claim 1 wherein the extension comprises superelastic nickel titanium alloy.

14. The catheter system of claim 1 further comprising a tubular outer sheath which is disposed over the endoluminal prosthesis and chassis and which includes an inner surface that constrains the endoluminal prosthesis in the constrained state.

15. The catheter system of claim 14 further comprising a nosecone secured to a distal end of the chassis, the nosecone including a shoulder portion which is disposed within a distal end of the tubular outer sheath and the shoulder portion further comprising a slot which is configured to accept the distal end of the extension when the extension is in the radially constrained state.

16. The catheter system of claim 1 wherein the chassis comprises a guidewire lumen extending from the proximal end of the chassis to the distal end of the chassis.

17. The catheter system of claim 1 wherein the tubular endoluminal prosthesis comprises a tubular stent graft including at least one layer of compliant material secured to a self-expanding stent.

18. The catheter system of claim 17 wherein the thin compliant material comprises ePTFE.

19. The catheter system of claim 17 wherein the stent graft comprises a fully stented stent graft.

\* \* \* \* \*